United States Patent
Palerm et al.

(10) Patent No.: US 11,191,896 B2
(45) Date of Patent: Dec. 7, 2021

(54) INFUSION DEVICES AND RELATED METHODS AND SYSTEMS FOR PREEMPTIVE ALERTING

(71) Applicant: MEDTRONIC MINIMED, INC., Northridge, CA (US)

(72) Inventors: Cesar C. Palerm, Pasadena, CA (US); Jeffrey C. Myers, Moorpark, CA (US)

(73) Assignee: Medtronic MiniMed, Inc., Northridge, CA (US)

(*) Notice: Subject to any disclaimer, the term of this patent is extended or adjusted under 35 U.S.C. 154(b) by 288 days.

(21) Appl. No.: 16/387,297

(22) Filed: Apr. 17, 2019

(65) Prior Publication Data
US 2019/0240403 A1     Aug. 8, 2019

Related U.S. Application Data

(62) Division of application No. 14/578,174, filed on Dec. 19, 2014, now Pat. No. 10,307,535.

(51) Int. Cl.
*A61M 5/172* (2006.01)
*A61M 5/168* (2006.01)
(Continued)

(52) U.S. Cl.
CPC ..... *A61M 5/16831* (2013.01); *A61B 5/14532* (2013.01); *A61B 5/4839* (2013.01);
(Continued)

(58) Field of Classification Search
CPC ............ A61M 5/16831; A61M 5/1723; A61B 5/14532; A61B 5/4839; A61B 5/7275
(Continued)

(56) References Cited

U.S. PATENT DOCUMENTS 3,631,847 A   1/1972   Hobbs, II
4,212,738 A   7/1980   Henne
(Continued)

FOREIGN PATENT DOCUMENTS

DE   4329229   3/1995
EP   0319268   11/1988
(Continued)

OTHER PUBLICATIONS (Animas Corporation, 1999). Animas . . . bringing new life to insulin therapy. (Applicant points out, in accordance with MPEP 609.04(a), that the year of publication, 1999 is sufficiently earlier than the effective U.S. filing date, so that the particular month of publication is not in issue.).

(Continued)

*Primary Examiner* — Phillip A Gray
(74) *Attorney, Agent, or Firm* — Shumaker & Sieffert, P.A.

(57) ABSTRACT

Infusion systems, infusion devices, and related operating methods are provided. An exemplary method of alerting a user associated with an infusion device delivering fluid to the body of the user involves obtaining a measurement value for a physiological condition being influenced by the fluid, obtaining a current amount of active fluid in the body of the user, determining a homeostasis metric based at least in part on the current amount of active fluid and the measurement value for the physiological condition, and generating an alert based at least in part on the homeostasis metric.

19 Claims, 11 Drawing Sheets

(51) Int. Cl.
*A61B 5/145* (2006.01)
*A61B 5/00* (2006.01)
*G16H 20/17* (2018.01)

(52) U.S. Cl.
CPC ......... *A61B 5/7275* (2013.01); *A61M 5/1723* (2013.01); *G16H 20/17* (2018.01); *A61M 2205/18* (2013.01)

(58) Field of Classification Search
USPC ........................................................ 604/504
See application file for complete search history.

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen |
| 4,755,173 A | 7/1988 | Konopka et al. |
| 4,781,798 A | 11/1988 | Gough |
| 4,803,625 A | 2/1989 | Fu et al. |
| 4,809,697 A | 3/1989 | Causey et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,522,803 A | 6/1996 | Teissen-Simony |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Martiila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,807,375 A | 9/1998 | Gross et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,954,643 A | 9/1999 | Van Antwerp et al. |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,017,328 A | 1/2000 | Fischell et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |

(56) References Cited

U.S. PATENT DOCUMENTS

| | | |
|---|---|---|
| 6,183,412 B1 | 2/2001 | Benkowski et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,259,937 B1 | 7/2001 | Schulman et al. |
| 6,329,161 B1 | 12/2001 | Heller et al. |
| 6,355,021 B1 | 3/2002 | Nielsen et al. |
| 6,379,301 B1 | 4/2002 | Worthington et al. |
| 6,408,330 B1 | 6/2002 | Delahuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,544,212 B2 | 4/2003 | Galley et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,591,876 B2 | 7/2003 | Safabash |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,723,046 B2 | 4/2004 | Lichtenstein et al. |
| 6,728,576 B2 | 4/2004 | Thompson et al. |
| 6,733,471 B1 | 5/2004 | Ericson et al. |
| 6,736,797 B1 | 5/2004 | Larsen et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,587 B2 | 6/2004 | Flaherty |
| 6,749,740 B2 | 6/2004 | Liamos et al. |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,153,263 B2 | 12/2006 | Carter et al. |
| 7,153,289 B2 | 12/2006 | Vasko |
| 7,303,549 B2 | 12/2007 | Flaherty et al. |
| 7,323,142 B2 | 1/2008 | Pendo et al. |
| 7,396,330 B2 | 7/2008 | Banet et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 8,674,288 B2 | 3/2014 | Hanson et al. |
| 10,307,535 B2 | 6/2019 | Palerm et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0015132 A1 | 1/2004 | Brown |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey et al. |
| 2004/0074785 A1 | 4/2004 | Holker et al. |
| 2004/0093167 A1 | 5/2004 | Braig et al. |
| 2004/0097796 A1 | 5/2004 | Berman et al. |

(56) References Cited

U.S. PATENT DOCUMENTS

| | | | |
|---|---|---|---|
| 2004/0102683 A1 | 5/2004 | Khanuja et al. | |
| 2004/0111017 A1 | 6/2004 | Say et al. | |
| 2004/0122353 A1 | 6/2004 | Shahmirian et al. | |
| 2004/0167465 A1 | 8/2004 | Mihal et al. | |
| 2004/0263354 A1 | 12/2004 | Mann et al. | |
| 2005/0038331 A1 | 2/2005 | Silaski et al. | |
| 2005/0038680 A1 | 2/2005 | McMahon et al. | |
| 2005/0154271 A1 | 7/2005 | Rasdal et al. | |
| 2005/0192557 A1 | 9/2005 | Brauker et al. | |
| 2006/0229694 A1 | 10/2006 | Schulman et al. | |
| 2006/0238333 A1 | 10/2006 | Welch et al. | |
| 2006/0293571 A1 | 12/2006 | Bao et al. | |
| 2007/0088521 A1 | 4/2007 | Shmuel et al. | |
| 2007/0123819 A1 | 5/2007 | Mernoe et al. | |
| 2007/0135866 A1 | 6/2007 | Baker et al. | |
| 2008/0154503 A1 | 6/2008 | Wittenber et al. | |
| 2009/0058635 A1 | 3/2009 | LaLonde et al. | |
| 2009/0081951 A1 | 3/2009 | Erdmann et al. | |
| 2009/0082635 A1 | 3/2009 | Baldus et al. | |
| 2010/0057042 A1* | 3/2010 | Hayter | A61B 5/7275 604/504 |
| 2010/0160861 A1 | 6/2010 | Causey, III et al. | |
| 2013/0030358 A1* | 1/2013 | Yodfat | A61M 5/1413 604/66 |
| 2014/0107607 A1 | 4/2014 | Estes | |
| 2015/0165117 A1 | 6/2015 | Palerm et al. | |
| 2015/0217051 A1 | 8/2015 | Mastrototaro et al. | |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 9620745 | 7/1996 |
| WO | WO 9636389 | 11/1996 |
| WO | WO 9637246 A1 | 11/1996 |
| WO | WO 9721456 | 6/1997 |
| WO | WO 9820439 | 5/1998 |
| WO | WO 9824358 | 6/1998 |
| WO | WO 9842407 | 10/1998 |
| WO | WO 9849659 | 11/1998 |
| WO | WO 9859487 | 12/1998 |
| WO | WO 9908183 | 2/1999 |
| WO | WO 9910801 | 3/1999 |
| WO | WO 9918532 | 4/1999 |
| WO | WO 9922236 | 5/1999 |
| WO | WO 0010628 | 3/2000 |
| WO | WO 0019887 | 4/2000 |
| WO | WO 0048112 | 8/2000 |
| WO | WO 02058537 | 8/2002 |
| WO | WO 03001329 | 1/2003 |
| WO | WO 03094090 | 11/2003 |
| WO | WO 2005065538 | 7/2005 |

OTHER PUBLICATIONS (Intensive Diabetes Management, 1995). Insulin Infusion Pump Therapy. pp. 66-78. (Applicant points out, in accordance with MPEP 609.04(a), that the year of publication, 1995 is sufficiently earlier than the effective U.S. filing date, so that the particular month of publication is not in issue.).

(Medtronic MiniMed, 2002). Medtronic MiniMed Meal Bolus Calculator and Correction Bolus Calculator. International Version. (Applicant points out, in accordance with MPEP 609.04(a), that the year of publication, 2002 is sufficiently earlier than the effective U.S. filing date, so that the particular month of publication is not in issue.).

(Medtronic MiniMed, 2002). The 508 Insulin Pump A Tradition of Excellence. (Applicant points out, in accordance with MPEP 609. 04(a), that the year of publication, 2002 is sufficiently earlier than the effective U.S. filing date, so that the particular month of publication is not in issue.).

(MiniMed Inc. 1999). MiniMed 508 Flipchart Guide to Insulin Pump Therapy. (Applicant points out, in accordance with MPEP 609.04(a), that the year of publication, 1999 is sufficiently earlier than the effective U.S. filing date, so that the particular month of publication is not in issue.).

(MiniMed Inc., 1999). Insulin Pump Comparison I Pump Therapy Will Change Your Life. (Applicant points out, in accordance with MPEP 609.04(a), that the year of publication, 1999 is sufficiently earlier than the effective U.S. filing date, so that the particular month of publication is not in issue.).

(MiniMed Inc., 2000). MiniMed® Now [I] Can Meal Bolus Calculator I MiniMed® Now [I] Can Correction Bolus Calculator. (Applicant points out, in accordance with MPEP 609.04(a), that the year of publication, 2000 is sufficiently earlier than the effective U.S. filing date, so that the particular month of publication is not in issue.).

(MiniMed Inc., 2000). Now [I] Can MiniMed Diabetes Management. (Applicant points out, in accordance with MPEP 609.04(a), that the year of publication, 2000 is sufficiently earlier than the effective U.S. filing date, so that the particular month of publication is not in issue.).

(MiniMed Inc., 2000). Now [I] Can MiniMed Pump Therapy. (Applicant points out, in accordance with MPEP 609.04(a), that the year of publication, 2000 is sufficiently earlier than the effective U.S. filing date, so that the particular month of publication is not in issue.).

(MiniMed International, 1998). MiniMed 507C Insulin Pump For those who appreciate the difference. (Applicant points out, in accordance with MPEP 609.04(a), that the year of publication, 1998 is sufficiently earlier than the effective U.S. filing date, so that the particular month of publication is not in issue.).

(MiniMed Technologies, 1994). MiniMed 506 Insulin Pump User's Guide. (Applicant points out, in accordance with MPEP 609.04(a), that the year of publication, 1994 is sufficiently earlier than the effective U.S. filing date, so that the particular month of publication is not in issue.).

(MiniMed Technologies, 1994). MiniMedrM Dosage Calculator Initial Meal Bolus Guidelines I MiniMed™ Dosage Calculator Initial Basal Rate Guidelines Percentage Method. 4 pages. (Applicant points out, in accordance with MPEP 609.04(a), that the year of publication, 1994 is sufficiently earlier than the effective U.S. filing date, so that the particular month of publication is not in issue.).

(MiniMed, 1996). FAQ: The Practical Things . . . pp. 1-4. Retrieved on Sep. 16, 2003 from the WOrld Wide Web: http://web.archive. orglwebl19961111054546/www.minimed.com/fileslfaq_pract.htm. (Applicant points out, in accordance with MPEP 609.04(a), that the year of publication, 1996 is sufficiently earlier than the effective U.S. filing date, so that the particular month of publication is not in issue.).

(MiniMed, 1996). MiniMedTM 507Insulin Pump User's Guide. (Applicant points out, in accordance with MPEP 609.04(a), that the year of publication, 1996 is sufficiently earlier than the effective U.S. filing date, so that the particular month of publication is not in issue.).

(MiniMed, 1996). The MiniMed 506. 7 pages. Retrieved on Sep. 16, 2003 from the WOrld Wide Web: http:/lweb.archive.orglweb/ 19961111054527/www.minimed.comlfiles/506_pic.htm.

(MiniMed, 1997). MiniMed 507 Specifications. 2 pages. Retrieved on Sep. 16, 2003 from the WOrld Wide Web: http://web.archive. org/web/199701242348411www.minimed.comlfileslmmn075.htm.

(MiniMed, 1997). MiniMedrM 507 Insulin Pump User's Guide. (Applicant points out, in accordance with MPEP 609.04(a), that the year of publication, 1997 is sufficiently earlier than the effective U.S. filing date, so that the particular month of publication is not in issue.).

(MiniMed, 1997). Wanted: a Few Good Belt Clips! 1 page. Retrieved on Sep. 16, 2003 from the WOrld Wide Web: http:l/web.archive. orglwebl199701242345591www.minimed.comlfileslmmn002.htm.

(MiniMed, 1998). MiniMed 507C Insulin Pump User's Guide. (Applicant points out, in accordance with MPEP 609.04(a), that the

(56) References Cited

OTHER PUBLICATIONS year of publication, 1998 is sufficiently earlier than the effective U.S. filing date, so that the particular month of publication is not in issue.).

(MiniMed, 2000). MiniMed® 508 User's Guide. (Applicant points out, in accordance with MPEP 609.04(a), that the year of publication, 2000 is sufficiently earlier than the effective U.S. filing date, so that the particular month of publication is not in issue.).

Abel, P., et al., "Experience with an implantable glucose sensor as a prerequiste of an artificial beta cell," Biomed. Biochim. Acta 43 (1984) 5, pp. 577-584. (Applicant points out, in accordance with MPEP 609.04(a), that the year of publication, 1984 is sufficiently earlier than the effective U.S. filing date, so that the particular month of publication is not in issue.).

Bindra, Dilbir S., et al., "Design and in Vitro Studies of a Needle-Type Glucose Sensor for a Subcutaneous Monitoring," American Chemistry Society, 1991, 63, pp. 1692-1696. (Applicant points out, in accordance with MPEP 609.04(a), that the year of publication, 1991 is sufficiently earlier than the effective U.S. filing date, so that the particular month of publication is not in issue.).

Bode B W, et al. (1996). Reduction in Severe Hypoglycemia with Long-Term Continuous Subcutaneous Insulin Infusion in Type I Diabetes. Diabetes Care, vol. 19, No. 4, 324-327. (Applicant points out, in accordance with MPEP 609.04(a), that the year of publication, 1984 is sufficiently earlier than the effective U.S. filing date, so that the particular month of publication is not in issue.).

Boguslavsky, Leonid, et al., "Applications of redox polymers in biosensors," Sold State Ionics 60, 1993, pp. 189-197. (Applicant points out, in accordance with MPEP 609.04(a), that the year of publication, 1993 is sufficiently earlier than the effective U.S. filing date, so that the particular month of publication is not in issue.).

Boland E (1998). Teens Pumping it Up! Insulin Pump Therapy Guide for Adolescents. 2nd Edition. (Applicant points out, in accordance with MPEP 609.04(a), that the year of publication, 1998 is sufficiently earlier than the effective U.S. filing date, so that the particular month of publication is not in issue.).

Brackenridge B P (1992). Carbohydrate Gram Counting A Key to Accurate Mealtime Boluses in Intensive Diabetes Therapy. Practical Diabetology, vol. 11, No. 2, pp. 22-28. (Applicant points out, in accordance with MPEP 609.04(a), that the year of publication, 1992 is sufficiently earlier than the effective U.S. filing date, so that the particular month of publication is not in issue.).

Brackenridge, B P et al. (1995). Counting Carbohydrates How to Zero in on Good Control. MiniMed Technologies Inc. (Applicant points out, in accordance with MPEP 609.04(a), that the year of publication, 1995 is sufficiently earlier than the effective U.S. filing date, so that the particular month of publication is not in issue.).

Disetronic H-TRON® plus Quick Start Manual. (no date).

Disetronic H-TRON® plus Reference Manual. (no date).

Disetronic My Choice H-TRONplus Insulin Pump Reference Manual. (no date).

Disetronic My Choice™ D-TRONTM Insulin Pump Reference Manual. (no date).

Farkas-Hirsch Ret al. (1994). Continuous Subcutaneous Insulin Infusion: A Review of the Past and Its Implementation for the Future. Diabetes Spectrum From Research to Practice, vol. 7, No. 2, pp. 80-84, 136-138. (Applicant points out, in accordance with MPEP 609.04(a), that the year of publication, 1994 is sufficiently earlier than the effective U.S. filing date, so that the particular month of publication is not in issue.).

Geise, Robert J., et al., "Eiectropolymerized 1,3-diaminobenzene for the construction of a 1,1'-dimethylferrocene mediated glucose biosensor," Analytica Chimica Acta, 2B1, 1993, pp. 467-473. (Applicant points out, in accordance with MPEP 609.04(a), that the year of publication, 1993 is sufficiently earlier than the effective U.S. filing date, so that the particular month of publication is not in issue.).

Gernet, S., et al., "A Planar Glucose Enzyme Electrode," Sensors and Actuators, 17, 1989, pp. 537-540. (Applicant points out, in accordance with MPEP 609.04(a), that the year of publication, 1989 is sufficiently earlier than the effective U.S. filing date, so that the particular month of publication is not in issue.).

Gernet, S., et al., "Fabrication and Characterization of a Planar Electromechanical Cell and its Application as a Glucose Sensor," Sensors and Actuators, 18, 1989, pp. 59-70. (Applicant points out, in accordance with MPEP 609.04(a), that the year of publication, 1989 is sufficiently earlier than the effective U.S. filing date, so that the particular month of publication is not in issue.).

Gorton, L., et al., "Amperometric Biosensors Based on an Apparent Direct Electron Transfer Between Electrodes and Immobilized Peroxiases," Analyst, Aug. 1991, vol. 117, pp. 1235-1241. (Applicant points out, in accordance with MPEP 609.04(a), that the year of publication, 1991 is sufficiently earlier than the effective U.S. filing date, so that the particular month of publication is not in issue.).

Gorton, L., et al., "Amperometric Glucose Sensors Based on Immobilized Glucose-Oxidizing Enymes and Chemically Modified Electrodes," Analytica Chimica Acta, 249, 1991, pp. 43-54. (Applicant points out, in accordance with MPEP 609.04(a), that the year of publication, 1991 is sufficiently earlier than the effective U.S. filing date, so that the particular month of publication is not in issue.).

Gough, D. A., et al., "Two-Dimensional Enzyme Electrode Sensor for Glucose," Analytical Chemistry, vol. 57, No. 5, 1985, pp. 2351-2357. (Applicant points out, in accordance with MPEP 609.04(a), that the year of publication, 1985 is sufficiently earlier than the effective U.S. filing date, so that the particular month of publication is not in issue.).

Gregg, Brian A., et al., "Cross-Linked Redox Gels Containing Glucose Oxidase for Amperometric Biosensor Applications," Analytical Chemistry, 62, Feb. 1990, pp. 258-263.

Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975. (Applicant points out, in accordance with MPEP 609.04(a), that the year of publication, 1991 is sufficiently earlier than the effective U.S. filing date, so that the particular month of publication is not in issue.).

Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.

Heller, Adam, "Electrical Wiring of Redox Enzymes," Ace. Chern. Res., vol. 23, No. 5, May 1990, pp. 128-134.

Hirsch I B et al. (1990). Intensive Insulin Therapy for Treatment of Type I Diabetes. Diabetes Care, vol. 13, No. 12, pp. 1265-1283. (Applicant points out, in accordance with MPEP 609.04(a), that the year of publication, 1990 is sufficiently earlier than the effective U.S. filing date, so that the particular month of publication is not in issue.).

Jobst, Gerhard, et al., "Thin-Film Microbiosensors for Glucose-Lactate Monitoring," Analytical Chemistry, vol. 68, No. 18, Sep. 15, 1996, pp. 3173-3179.

Johnson, K.W., et al., "In vivo evaluation of an electroenzymatic glucose sensor implanted in subcutaneous tissue," Biosensors & Bioelectronics, 7, 1992, pp. 709-714. (Applicant points out, in accordance with MPEP 609.04(a), that the year of publication, 1992 is sufficiently earlier than the effective U.S. filing date, so that the particular month of publication is not in issue.).

Jonsson, G., et al., "An Electromechanical Sensor for Hydrogen Peroxide Based on Peroxidase Adsorbed on a Spectrographic Graphite Electrode," Electroanalysis, 1989, pp. 465-468. (Applicant points out, in accordance with MPEP 609.04(a), that the year of publication, 1989 is sufficiently earlier than the effective U.S. filing date, so that the particular month of publication is not in issue.).

Kanapieniene, J. J., et al., "Miniature Glucose Biosensor with Extended Linearity," Sensors and Actuators, B. 10, 1992, pp. 37-40. (Applicant points out, in accordance with MPEP 609.04(a), that the year of publication, 1992 is sufficiently earlier than the effective U.S. filing date, so that the particular month of publication is not in issue.).

(56) References Cited

OTHER PUBLICATIONS

Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52. (Applicant points out, in accordance with MPEP 609.04(a), that the year of publication, 1988 is sufficiently earlier than the effective U.S. filing date, so that the particular month of publication is not in issue.).
Koudelka, M., et al., "In-vivo Behaviour of Hypodermically Implanted Microfabricated Glucose Sensors," Biosensors & Bioelectronics 6, 1991, pp. 31-36. (Applicant points out, in accordance with MPEP 609.04(a), that the year of publication, 1991 is sufficiently earlier than the effective U.S. filing date, so that the particular month of publication is not in issue.).
Koudelka, M., et al., "Planar Amperometric Enzyme-Based Glucose Microelectrode," Sensors & Actuators, 18, 1989, pp. 157-165. (Applicant points out, in accordance with MPEP 609.04(a), that the year of publication, 1991 is sufficiently earlier than the effective U.S. filing date, so that the particular month of publication is not in issue.).
Kulkarni Ket al. (1999). Carbohydrate Counting A Primer for Insulin Pump Users to Zero in on Good Control. MiniMed Inc. (Applicant points out, in accordance with MPEP 609.04(a), that the year of publication, 1999 is sufficiently earlier than the effective U.S. filing date, so that the particular month of publication is not in issue.).
Marcus A 0 et al. (1996). Insulin Pump Therapy Acceptable Alternative to Injection Therapy. Postgraduate Medicine, vol. 99, No. 3, pp. 125-142. (Applicant points out, in accordance with MPEP 609.04(a), that the year of publication, 1996 is sufficiently earlier than the effective U.S. filing date, so that the particular month of publication is not in issue.).
Mastrototaro, John J., et al. "An electroenzymatic glucose sensor fabricated on a flexible substrate," Sensors & Actuators, B. 5,1991, pp. 139-144. (Applicant points out, in accordance with MPEP 609.04(a), that the year of publication, 1991 is sufficiently earlier than the effective U.S. filing date, so that the particular month of publication is not in issue.).
Mastrototaro, John J., et al., "An Electroenzymatic Sensor Capable of 72 Hour Continuous Monitoring of Subcutaneous Glucose," 14th Annual International Diabetes Federation Congress, Washington D.C.. Jun. 23-28, 1991.
Mckean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," AnnuaaIInternational Conference ofteh IEEE Engineering in Medicine and Biology Society, Vo. 12, No. 2, 1990, pp. 483-484. (Applicant points out, in accordance with MPEP 609.04(a), that the year of publication, 1999 is sufficiently earlier than the effective U.S. filing date, so that the particular month of publication is not in issue.).
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172. (Applicant points out, in accordance with MPEP 609.04(a), that the year of publication, 1988 is sufficiently earlier than the effective U.S. filing date, so that the particular month of publication is not in issue.).
Nishida, Kenro, et al., "Clinical applications often wearable artificial endocrine pancreas with the newly designed needle-type glucose sensor," Elsevier Sciences B.V., 1994, pp. 353-358. (Applicant points out, in accordance with MPEP 609.04(a), that the year of publication, 1994 is sufficiently earlier than the effective U.S. filing date, so that the particular month of publication is not in issue.).
Nishida, Kenro, et al., "Development of a ferrocene-mediated needle-type glucose sensor covered with newly designed biocompatible membrane, 2-methacryloyloxyethylphosphorylcholine-co-n-butyl methacrylate," Medical Progress Through Technology, vol. 21, 1995, pp. 91-103. (Applicant points out, in accordance with MPEP 609.04(a), that the year of publication, 1995 is sufficiently earlier than the effective U.S. filing date, so that the particular month of publication is not in issue.).
Poitout, V., et al., "A glucose monitoring system for on line estimation on man of blood glucose concentration using a miniaturized glucose sensor implanted in the subcutaneous tissue and a wearable control unit," Diabetologia, vol. 36, published Jul. 1993, pp. 658-663.
Reach, G., "A Method for Evaluating in vivo the Functional Characteristics of Glucose Sensors," Biosensors 2, 1986, pp. 211-220. (Applicant points out, in accordance with MPEP 609.04(a), that the year of publication, 1986 is sufficiently earlier than the effective U.S. filing date, so that the particular month of publication is not in issue.).
Reed J et al. (1996). Voice of the Diabetic, vol. 11, No. 3, pp. 1-38. (Applicant points out, in accordance with MPEP 609.04(a), that the year of publication, 1986 is sufficiently earlier than the effective U.S. filing date, so that the particular month of publication is not in issue.).
Shaw, G. W., et al., "In vitro testing of a simply constructed, highly stable glucose sensor suitable for implantation in diabetic patients," Biosensors & Bioelectronics 6, 1991, pp. 401-406. (Applicant points out, in accordance with MPEP 609.04(a), that the year of publication, 1991 is sufficiently earlier than the effective U.S. filing date, so that the particular month of publication is not in issue.).
Shichiri, M., "A Needle-Type Glucose Sensor—A Valuable Tool Not Only For a Self-Blood Glucose Monitoring but for a Wearable Artificial Pancreas," Life Support Systems Proceedings, XI Annual Meeting ESAO, Alpbach-lnnsbruck, Austria, Sep. 1984, pp. 7-9.
Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20. (Applicant points out, in accordance with MPEP 609.04(a), that the year of publication, 1998 is sufficiently earlier than the effective U.S. filing date, so that the particular month of publication is not in issue.).
Shichiri, M., et al., "Membrane design for extending the long-life of an implantable glucose sensor," Diab. Nutr. Metab., vol. 2, No. 4, 1989, pp. 309-313. (Applicant points out, in accordance with MPEP 609.04(a), that the year of publication, 1991 is sufficiently earlier than the effective U.S. filing date, so that the particular month of publication is not in issue.).
Shichiri, Motoaki, et al., "An artificial endocrine pancreas—problems awaiting solution for long-term clinical applications of a glucose sensor," Frontiers Med. Bioi. Engng., 1991, vol. 3, No. 4, pp. 283-292. (Applicant points out, in accordance with MPEP 609.04(a), that the year of publication, 1998 is sufficiently earlier than the effective U.S. filing date, so that the particular month of publication is not in issue.).
Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.
Shichiri, Motoaki, et al., "Giycaemic Control in a Pacreatectomized Dogs with a Wearable Artificial Endocrine Pancreas," Diabetologia, vol. 24, 1983, pp. 179-184. (Applicant points out, in accordance with MPEP 609.04(a), that the year of publication, 1983 is sufficiently earlier than the effective U.S. filing date, so that the particular month of publication is not in issue.).
Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

(56) References Cited

OTHER PUBLICATIONS

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.
Shichiri, Motoaki, et al., "The Wearable Artificial Endocrine Pancreas with a Needle-Type Glucose Sensor: Perfect Glycemic Control in Ambulatory Diabetes," Acta Paediatr Jpn, Dec. 1984, vol. 26, pp. 359-370.
Shichiri, Motoaki, et al., "Wearable Artificial Endocrine Pancreas with Needle-Type Glucose Sensor," The Lancet, Nov. 20, 1992, pp. 1129-1131.
Shinkai, Seiji, "Molecular Recognitiion of Mono- and Di-saccharides by Phenylboronic Acids in Solvent Extraction and as a Monolayer," J. Chem. Soc., Chem. Commun., 1991, pp. 1039-1041. (Applicant points out, in accordance with MPEP 609.04(a), that the year of publication, 1991 is sufficiently earlier than the effective U.S. filing date, so that the particular month of publication is not in issue.).
Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.
Skyler J S, "Continuous Subcutaneous Insulin Infusion [CSII] With External Devices: Current Status. Update in Drug Delivery Systems," Chapter 13, pp. 163-183, 1989, Futura Publishing Company. (Applicant points out, in accordance with MPEP 609.04(a), that the year of publication, 1989 is sufficiently earlier than the effective U.S. filing date, so that the particular month of publication is not in issue.).
Skyler J S et al. (1995). The Insulin Pump Therapy Book Insights from the Experts. MiniMed Technologies, (Applicant points out, in accordance with MPEP 609.04(a), that the year of publication, 1995 is sufficiently earlier than the effective U.S. filing date, so that the particular month of publication is not in issue.).
Sternberg, Robert, et al., "Study and Development of Multilayer Needle-type Enzyme-based Glucose Microsensors," Biosensors, vol. 4, 1988, pp. 27-40. (Applicant points out, in accordance with MPEP 609.04(a), that the year of publication, 1988 is sufficiently earlier than the effective U.S. filing date, so that the particular month of publication is not in issue.).
Strowig S M (1993). Initiation and Management of Insulin Pump Therapy. The Diabetes Educator, vol. 19, No. 1, pp. 50-60. (Applicant points out, in accordance with MPEP 609.04(a), that the year of publication, 1993 is sufficiently earlier than the effective U.S. filing date, so that the particular month of publication is not in issue.).
Tamiya, E., et al., "Micro Glucose Sensors using Electron Mediators Immobilized on a Polypyrrole-Modified Electrode," Sensors and Actuators, vol. 18, 1989, pp. 297-307. (Applicant points out, in accordance with MPEP 609.04(a), that the year of publication, 1989 is sufficiently earlier than the effective U.S. filing date, so that the particular month of publication is not in issue.).
Tsukagoshi, Kazuhiko, et al., "Specific Complexation with Mono- and Disaccharides that can be Detected by Circular Dichroism," J. Org. Chem., vol. 56, 1991, pp. 4089-4091. (Applicant points out, in accordance with MPEP 609.04(a), that the year of publication, 1991 is sufficiently earlier than the effective U.S. filing date, so that the particular month of publication is not in issue.).
Ubran, G., et al., "Miniaturized thin-film biosensors using covalently immobilized glucose oxidase," Biosensors & Bioelectronics, vol. 6, 1991, pp. 555-562. (Applicant points out, in accordance with MPEP 609.04(a), that the year of publication, 1991 is sufficiently earlier than the effective U.S. filing date, so that the particular month of publication is not in issue.).
Urban, G., et al., "Miniaturized multi-enzyme biosensors integrated with pH sensors on flexible polymer carriers for in vivo applications," Biosensors & Bioelectronics, vol. 7, 1992, pp. 733-739. (Applicant points out, in accordance with MPEP 609.04(a), that the year of publication, 1992 is sufficiently earlier than the effective U.S. filing date, so that the particular month of publication is not in issue.).
Velho, G., et al., "In vivo calibration of a subcutaneous glucose sensor for determination of subcutaneous glucose kinetics," Diab. Nutr. Metab., vol. 3, 1988, pp. 227-233. (Applicant points out, in accordance with MPEP 609.04(a), that the year of publication, 1988 is sufficiently earlier than the effective U.S. filing date, so that the particular month of publication is not in issue.).
Walsh J, et al. (1989). Pumping Insulin: The Art of Using an Insulin Pump. Published by MiniMed Technologies. (Applicant points out, in accordance with MPEP 609.04(a), that the year of publication, 1989 is sufficiently earlier than the effective U.S. filing date, so that the particular month of publication is not in issue.).
Wang, Joseph, et al., "Needle-Type Dual Microsensor for the Simultaneous Monitoring of Glucose and Insulin," Analytical Chemistry, vol. 73, 2001, pp. 844-847. (Applicant points out, in accordance with MPEP 609.04(a), that the year of publication, 2001 is sufficiently earlier than the effective U.S. filing date, so that the particular month of publication is not in issue.).
Yamasaki, Yoshimitsu, et al., "Direct Measurement of Whole Blood Glucose by a Needle-Type Sensor," Clinics Chimica Acta, vol. 93, 1989, pp. 93-98. (Applicant points out, in accordance with MPEP 609.04(a), that the year of publication, 1989 is sufficiently earlier than the effective U.S. filing date, so that the particular month of publication is not in issue.).
Yokoyama, K., "Integrated Biosensor for Glucose and Galactose," Analytica Chimica Acta, vol. 218, 1989 pp. 137-142 (Applicant points out, in accordance with MPEP 609.04(a), that the year of publication, 1989 is sufficiently earlier than the effective U.S. filing date, so that the particular month of publication is not in issue.).
International Search Report from International Application No. PCT/US2002/03299, dated Dec. 31, 2002.
International Preliminary Examination Report from International Application No. PCT/US2002/03299, dated Jan. 22, 2003, 2 pp.
Prosecution History from U.S. Appl. No. 14/578,174 dated Jun. 15, 2017 through Jan. 24, 2019, 83 pp.

\* cited by examiner

INFUSION DEVICES AND RELATED METHODS AND SYSTEMS FOR PREEMPTIVE ALERTING

CROSS-REFERENCE TO RELATED APPLICATIONS

This application is a division of U.S. patent application Ser. No. 14/578,174, filed Dec. 19, 2014, which is related to the subject matter described in U.S. patent application Ser. No. 14/578,170, filed concurrently therewith, and now issued as U.S. Pat. No. 10,265,031.

TECHNICAL FIELD

Embodiments of the subject matter described herein relate generally to medical devices, and more particularly, embodiments of the subject matter relate to preemptively alerting a user during operation of a fluid infusion device.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a diabetic's condition, and hence, control schemes are being developed that allow insulin infusion pumps to monitor and regulate a user's blood glucose level in a substantially continuous and autonomous manner. Predictive algorithms may be utilized to provide estimations of the future blood glucose levels as an aid in regulating the blood glucose level. Predicted values may be utilized to notify users of potential hypoglycemic or hyperglycemic events. However, regulating blood glucose level is complicated by variations in the response time for the type of insulin being used along with each user's individual insulin response in conjunction with the variable nature (e.g., in terms of both the quantity and the timing or frequency) of the insulin being infused and the carbohydrates consumed by the user. Thus, while a predicted value may indicate a potential hypoglycemic or hyperglycemic event, in reality, the potential hypoglycemic or hyperglycemic event may be unlikely. In such situations, alerts generated based on predicted values may be non-actionable and of limited utility, which, in turn, can frustrate or annoy users and increase the likelihood that subsequent alerts are ignored or not promptly addressed. At the same time, alerts based solely on currently sensed glucose values may be provided too late to avoid a hypoglycemic or hyperglycemic event.

BRIEF SUMMARY

Embodiment of a method of alerting a user is provided. An exemplary method of alerting the user involves obtaining a measurement value for a physiological condition in a body of the user that is being influenced by a fluid delivered by an infusion device, obtaining a current amount of active fluid in the body of the user, determining a homeostasis metric based at least in part on the current amount of active fluid and the measurement value for the physiological condition, and generating an alert based at least in part on the homeostasis metric.

An embodiment of an infusion system is also provided. The infusion system includes a user interface, an infusion device operable to deliver fluid influencing a physiological condition to a body of a user, a sensing arrangement to obtain a measurement value for the physiological condition from the body of the user, and a control system to obtain the measurement value from the sensing arrangement, determine a homeostasis metric based at least in part on the measurement value and a current amount of active fluid in the body of the user, and generate an alert via the user interface based at least in part on the homeostasis metric.

An embodiment of an infusion device is also provided. The infusion device includes a user interface, a motor operable to deliver fluid influencing a physiological condition to a body of a user, and a control system coupled to the motor and the user interface. The control system operates the motor to deliver the fluid, obtains a measurement value for the physiological condition in the body of the user, determines a current amount of active fluid in the body of the user, determines an amount of fluid pending delivery to the body of the user, determines a homeostasis metric based at least in part on the current amount of active fluid, the amount of fluid pending delivery, and the measurement value, and provides a notification via the user interface based at least in part on the homeostasis metric.

In another embodiment, a method of alerting a user involves obtaining a first value for a physiological condition in a body of the user being influenced by a fluid delivered by an infusion device, determining a metric corresponding to a future physiological condition of the user based at least in part on the first value, and automatically generating a first alert based on the metric. After automatically generating the first alert, the method continues by obtaining a second value for the physiological condition of the user and automatically clearing the first alert based at least in part on the second value.

In yet another embodiment, an infusion device includes a user interface, a motor operable to deliver fluid influencing a physiological condition to a body of a user, and a control system coupled to the motor and the user interface. The control system operates the motor to deliver the fluid, obtains a first measurement value for the physiological condition in the body of the user, determines a metric corresponding to a future physiological condition of the user in the future based at least in part on the first measurement value, automatically generates a first alert via the user interface based on the metric, obtains a second value for the physiological condition of the user after automatically generating the first alert, and automatically clears the first alert from the user interface based at least in part on the second value.

Another embodiment of an infusion system includes a user interface, an infusion device operable to deliver fluid influencing a physiological condition to a body of a user, a sensing arrangement to obtain measurement values for the physiological condition from the body of the user, and a control system coupled to the user interface and the sensing arrangement. The control system obtains a first measurement value for the physiological condition from the sensing arrangement, determines a metric corresponding to a future physiological condition of the user based at least in part on the first measurement value, automatically generates a first alert via the user interface based on the metric, and after automatically generating the first alert, obtains a second measurement value for the physiological condition from the sensing arrangement and automatically clears the first alert based at least in part on the second measurement value.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

DETAILED DESCRIPTION

Figure 1:
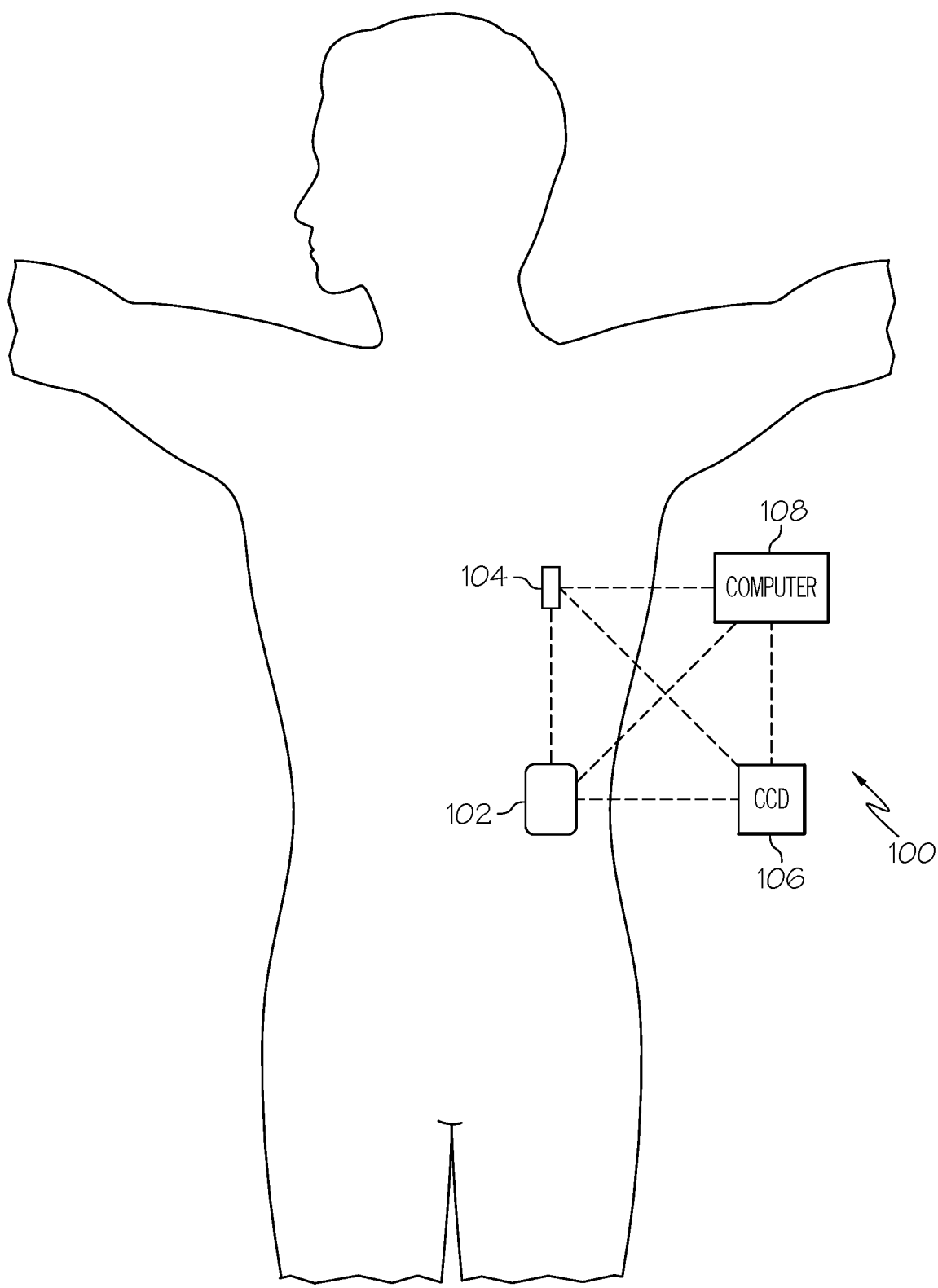
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to fluid infusion devices including a motor that is operable to linearly displace a plunger (or stopper) of a reservoir provided within the fluid infusion device to deliver a dosage of fluid, such as insulin, to the body of a user. The dosage commands that govern operation of the motor are influenced by a current (or most recent) measurement of a physiological condition in the body of the user, such as, for example, an interstitial fluid glucose level. In some embodiments, the dosage commands may also be influenced by a predicted value (or anticipated measurement) for that physiological condition in the body of the user at some point in the future. For example, an insulin dosage command may be determined based on a current blood glucose measurement for the user in a manner that is influenced by a predicted (or anticipated) blood glucose level in the body of the user 30 minutes into the future. In this regard, the insulin dosage command determined based on the user's current blood glucose level may be adjusted, modified, enabled and/or disabled based on the predicted blood glucose level. While the subject matter is described herein in the context of a fluid infusion device for purposes of explanation, the subject matter is not necessarily limited to such an implementation.

As described in greater detail below in the context of FIGS. 8-10, in exemplary embodiments, one or more homeostasis metrics indicative of the expected state of the physiological condition of the user in the future are determined and utilized to generate alerts or notifications regarding the user's physiological condition or the operational status of the infusion device. A homeostasis metric is representative of the relative balance between the current status of the fluid infusion and the current state of the user's physiological condition. For example, the value of a homeostasis metric may correspond to or otherwise be indicative of the expected glucose level of the user absent the user consuming additional carbohydrates or engaging in physical activity that would influence the user's glucose level. In exemplary embodiments, the value of a homeostasis metric is influenced by the current amount of previously-infused fluid that remains active within the user's body (e.g., the fluid yet to be metabolized or in the process of being metabolized), anticipated future deliveries of the fluid (e.g., pending or scheduled dosage commands that have not yet been implemented), and the current (or most recent) measurement value(s) indicative of the current state of the user's physiological condition. The resulting value of a homeostasis metric indicates whether the future physiological condition of the user will likely be at an acceptable level (or within an acceptable range of values) without any affirmative action by the user.

For example, the value of a homeostasis metric determined based on glucose measurement value(s) obtained from the body of the user, the current insulin on board (IOB) that is active in the body of the user, and anticipated future insulin deliveries may indicate the relative likelihood that the user's blood glucose will not exceed an upper threshold value (e.g., a hyperglycemic event) or fall below a lower threshold value (e.g., a hypoglycemic event). As described below, the homeostasis metric may be utilized to preemptively alert the user regarding a potential imbalance between the user's current IOB and the current user's glucose level such that the user can take remedial action to mitigate the potential imbalance and maintain his or her glucose level within an acceptable range. In this regard, the homeostasis metric may anticipate a potential hyperglycemic condition or a potential hypoglycemic condition or otherwise indicate an anomalous condition before the user would otherwise be notified based on the user's current glucose measurement values or predicted glucose values for the user. Alerting the user earlier increases the likelihood that any potential problems are mitigated in advance, and therefore, undesirable states of the user's physiological condition are less likely to occur. Additionally, the alerts generated based on the homeostasis metric values are likely to be actionable, and thus, are unlikely to frustrate or annoy users.

As described in greater detail below in the context of FIG. 8, in one or more embodiments, the homeostasis metric is an estimated correction bolus amount for maintaining the user's future glucose level at or near a target glucose level. An estimated amount of additional insulin is determined using the user's current glucose measurement value, the user's current IOB, any scheduled or pending future insulin deliveries, the user's current insulin sensitivity factor, and the target glucose value. The estimated correction bolus value is indicative of whether the user may need additional insulin to account for carbohydrates consumed by the user, physical activity (or lack thereof) by the user, or the like to maintain his or her glucose level at or near the target glucose value. In exemplary embodiments, the estimated correction bolus value is also dynamically adjusted based on the trend in the user's glucose measurement values. When the estimated correction bolus value exceeds a threshold value, the user is notified of the potential need to administer a correction bolus, and in some embodiments, the notification recommends administering a correction bolus having a dosage equal to the estimated correction bolus value.

The estimated correction bolus metric allows for alerts to be generated when an undesirably high glucose level (or a potential hyperglycemic event) is likely after accounting for the user's current IOB and scheduled insulin deliveries. At the same time, alerts are not generated when the estimated correction bolus metric indicates the glucose level will be at or near a desired target value. In this regard, while the user's predicted glucose level may indicate a potential hyperglycemic event, the estimated correction bolus metric may indicate that the current IOB and scheduled insulin deliveries will offset or otherwise counteract the potential hyperglycemic event and allow the user's glucose level to settle or otherwise achieve homeostasis at an acceptable level. Thus, the estimated correction bolus metric may be used to suppress or otherwise override any non-actionable alerts that would otherwise be generated based on the user's predicted glucose level. At the same time, the estimated correction bolus metric may indicate an undesirably high glucose level (or a potential hyperglycemic event) earlier than the user's predicted glucose level, and further, provide guidance regarding a recommended amount of insulin for a correction bolus that will likely mitigate the potentially high glucose level while the user's current glucose level and/or predicted glucose level is within an acceptable range of values.

As described in greater detail below in the context of FIG. 9, in another exemplary embodiment, the homeostasis metric is an expected glucose measurement value at a subsequent time after a correction bolus (or alternatively, the difference between the expected glucose measurement value at the subsequent time and the user's current glucose measurement value obtained at that subsequent time). In such embodiments, the homeostasis metric indicates that the correction bolus is not having its anticipated effect on the user's glucose level and that a potential anomalous condition exists. An expected drop in the user's current glucose measurement value to be observed at the subsequent time is determined based on the dosage amount for the correction bolus, any scheduled or pending future insulin deliveries if the bolus has an extended delivery time, the user's current IOB at the subsequent time, and the user's current insulin sensitivity factor. The expected glucose measurement value at the subsequent time is then determined based on the expected drop, the user's glucose measurement value at the time of the bolus, and the trend in the user's glucose measurement values at the time of the bolus.

When the difference between the expected glucose measurement value at the subsequent time and the user's current glucose measurement value obtained at that subsequent time is greater than a threshold amount, the homeostasis metric indicates that the correction bolus is not exhibiting the expected effect on the user's glucose level. In response, the user is notified of the potential anomalous condition causing the correction bolus to not have the anticipated effect on the user's glucose, thereby allowing the user to assess the operational status of the infusion device and fluid delivery path and/or administer an additional correction bolus to reduce the likelihood of a potential hyperglycemic event. When the correction bolus is not achieving the expected reduction in the user's glucose level, the user may be preemptively alerted to a potential hyperglycemic event based on the homeostasis metric while the user's current glucose level is within the acceptable range and/or the user's predicted future glucose level is within the acceptable range. Additionally, the homeostasis metric may be utilized to suppress or otherwise override any potentially non-actionable alerts that would otherwise be generated based on the user's predicted glucose level when the correction bolus is having the anticipated effect on the user's glucose.

As described in greater detail below in the context of FIG. 10, in yet another exemplary embodiment, the homeostasis metric is an estimated amount of excess insulin determined based on an expected glucose measurement value after all of the delivered insulin is metabolized. An expected drop in the user's glucose measurement value is determined based on the user's current IOB, any scheduled or pending future insulin deliveries, and the user's current insulin sensitivity factor. The expected glucose measurement value at is then determined based on the expected drop and the user's current glucose measurement value. The difference between the expected glucose measurement value and a glucose threshold value may be utilized to estimate an amount of excess insulin and generate a user notification that indicates or otherwise recommends the amount of carbohydrates to be consumed by the user to offset or otherwise compensate for the estimated amount of excess insulin. Additionally, or alternatively, an excess insulin alert may also notify the user of recommended modifications to the delivery scheme currently being implemented by the infusion device to mitigate the potential hypoglycemic event (e.g., temporarily reducing the basal infusion rate, suspending delivery, or the like), or recommend other remedial actions (e.g., a recommended dose of glucagon, recommending the user reduce physical activity or stop exercising, or the like).

When the homeostasis metric indicates excess insulin, the user may be preemptively alerted to a potential hypoglycemic event while the user's current glucose level is within the acceptable range and/or the user's predicted future glucose level is within the acceptable range. For example, the user's current glucose level may be within the acceptable range and the user's predicted future glucose level may be trending upward. However, the user may have inadvertently over-bolused for a meal, which could otherwise go undetected until the user's current and/or predicted future glucose level reverses direction and/or decreases by a sufficient amount, at which point, it may be too late to avoid a potential hypoglycemic event.

As described in greater detail below in the context of FIG. 11, in one or more exemplary embodiments, user notifications or alerts generated based on the homeostasis metric(s) may be automatically cleared based on subsequent measurement values that indicate either a reversal in the physiological condition of the user or presence of a higher severity (or higher priority) alert condition having the same root cause. For example, when an updated estimated correction bolus amount determined based on the most recently obtained glucose measurement value decreases below the alerting threshold value, the user notification indicating a recommended correction bolus may be automatically cleared or otherwise removed since the correction bolus amount is no longer desirable when the updated value indicates the user's glucose level is sufficiently likely to be maintained within the acceptable range. As such, the recommended correction bolus alert is automatically cleared when it is no longer actionable, thereby improving the user experience. Alternatively, if the most recently obtained glucose measurement value indicates the presence of a hyperglycemic event, the user notification indicating a recommended correction bolus may be automatically cleared or otherwise removed in lieu of a higher severity (or higher priority) alert. In this manner, the alerting is dynamic and adaptive in response to the current physiological condition of the user, and the user does not have to address multiple alerts having the same root cause (e.g., insufficient insulin delivery), which again, improves the user experience.

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. Pat. No. 8,674,288, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

As described above, in some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402, 153, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

Figure 2:
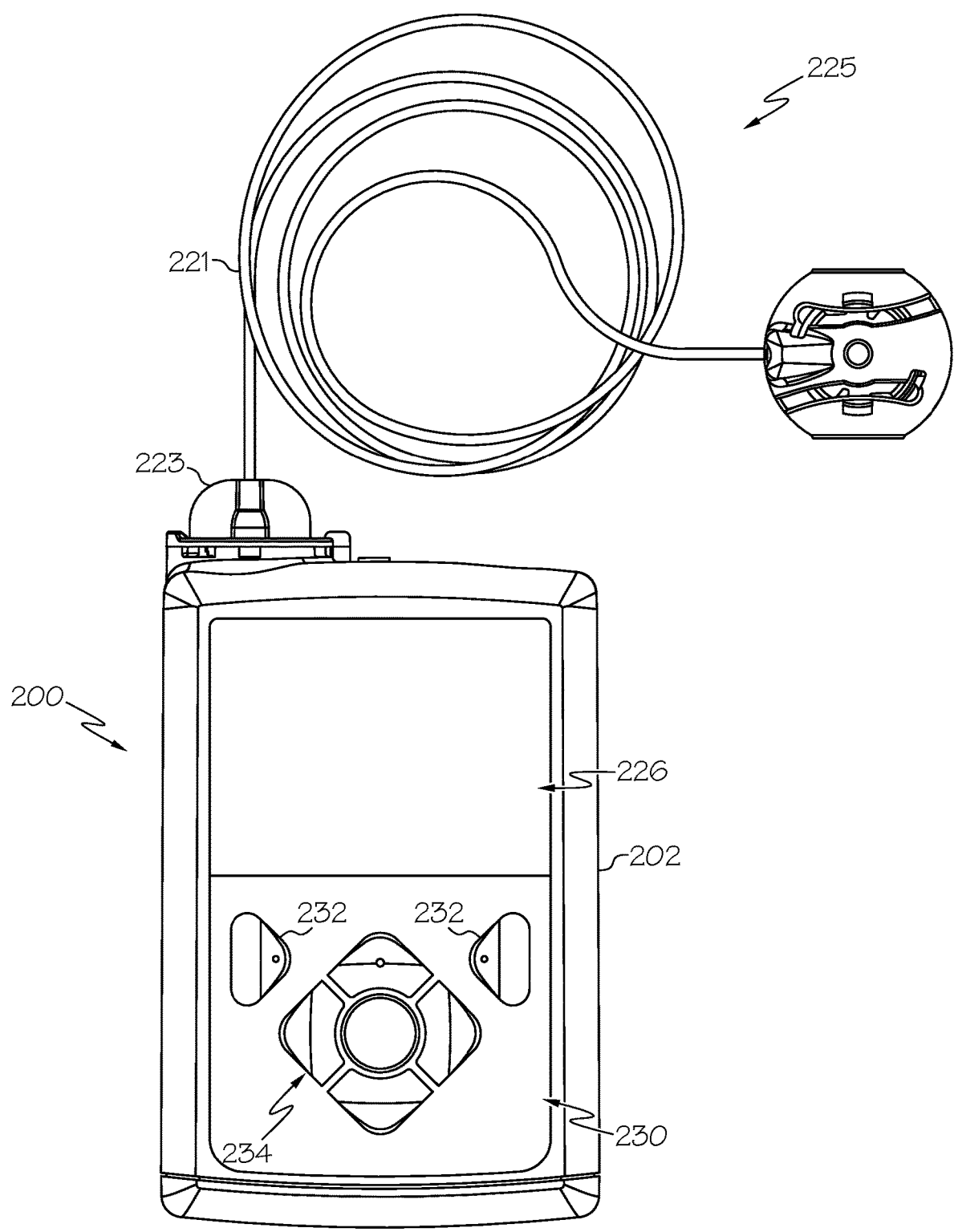
FIG. 2 depicts a plan view of an exemplary embodiment of a fluid infusion device suitable for use in the infusion system of FIG. 1.
Figure 3:
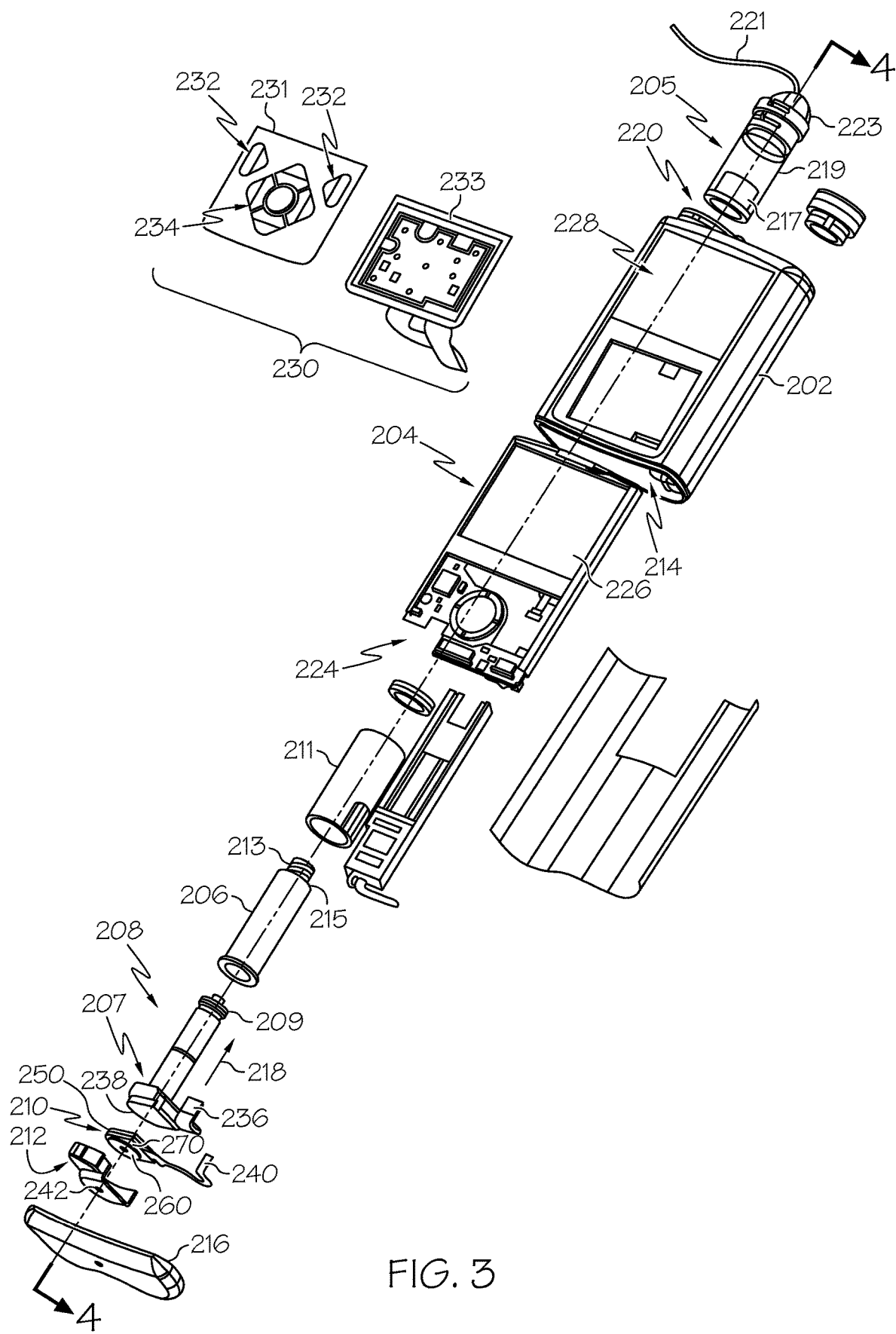
FIG. 3 is an exploded perspective view of the fluid infusion device of FIG. 2.
Figure 4:
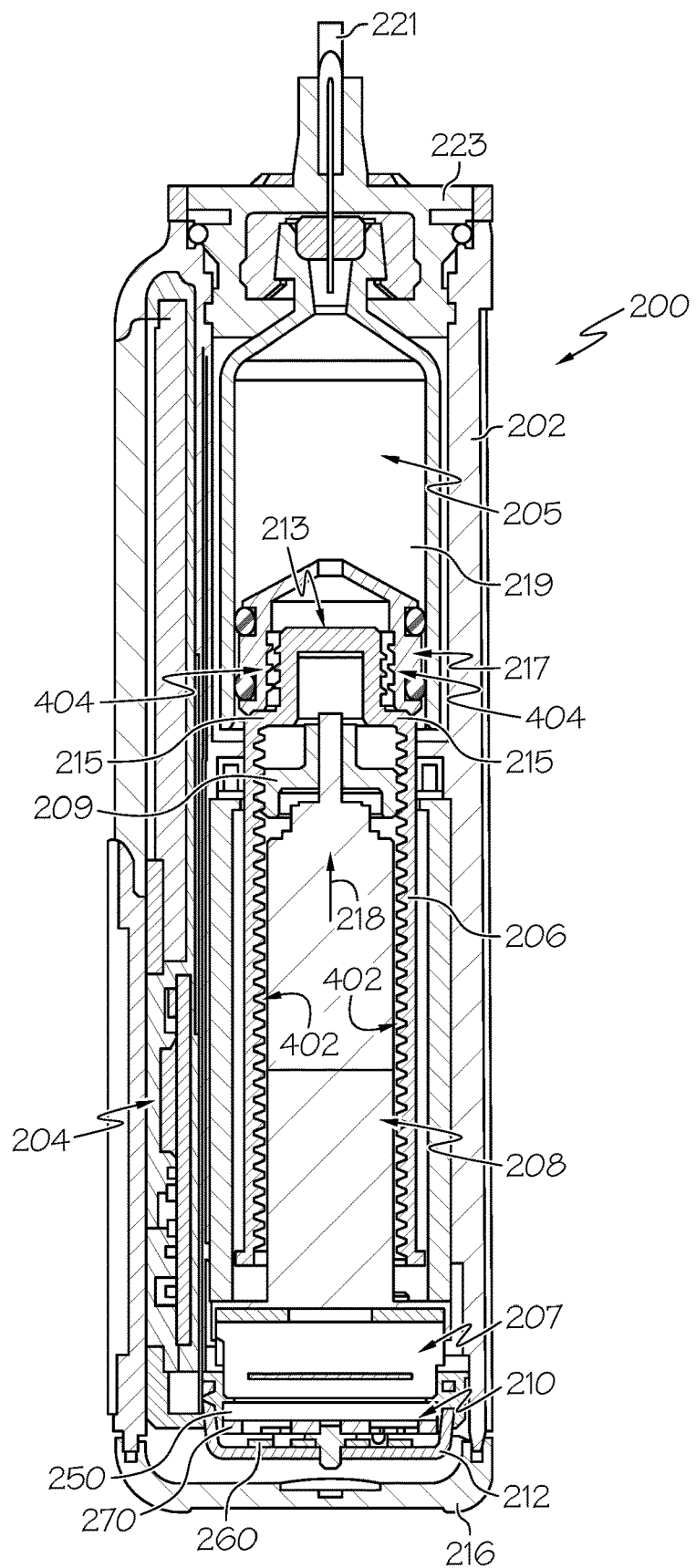
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. Pat. No. 8,474,332, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
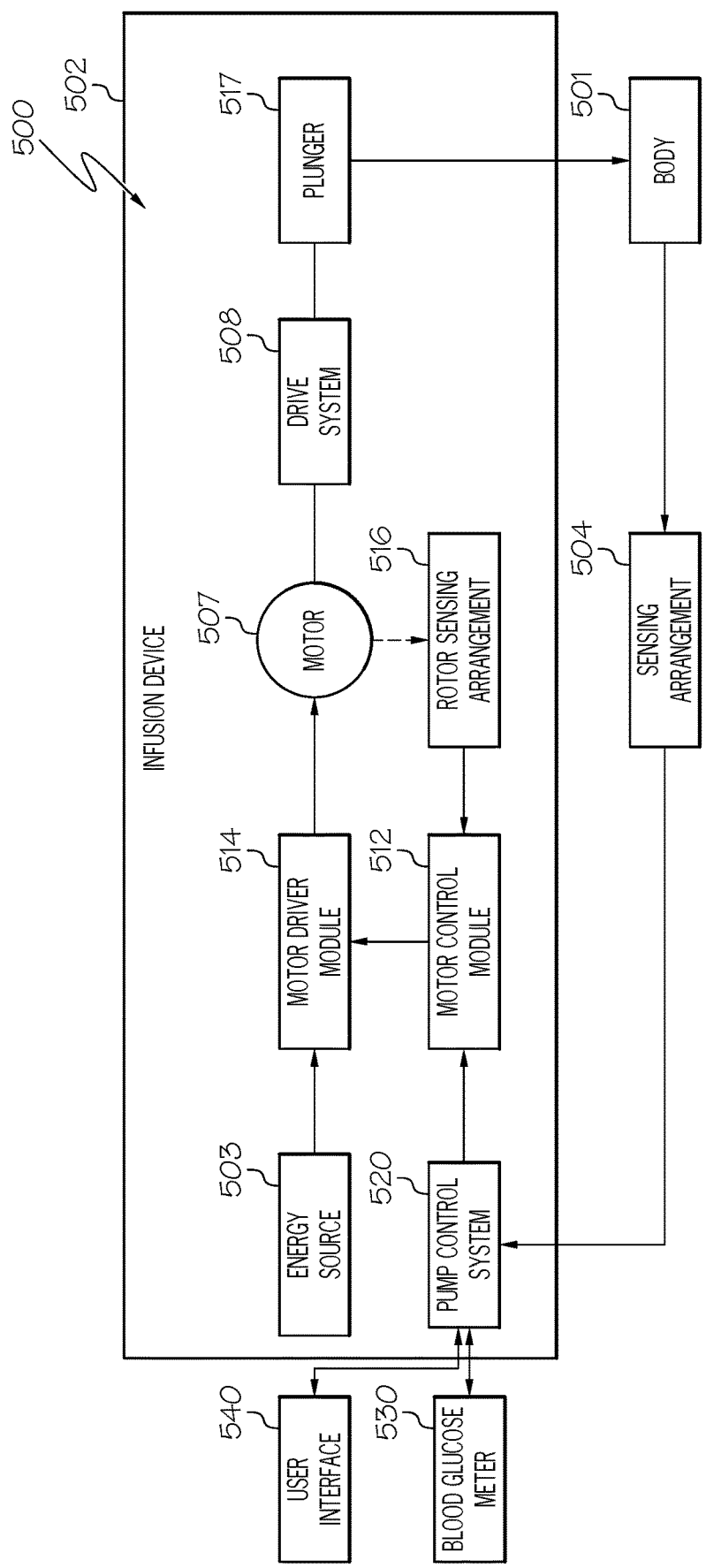
FIG. 5 is a block diagram of an exemplary control system suitable for use in a fluid infusion device, such as the fluid infusion device of FIG. 1 or FIG. 2.

FIG. 5 depicts an exemplary embodiment of a control system 500 suitable for use with an infusion device 502, such as the infusion device 102 in FIG. 1 or the infusion device 200 of FIG. 2. The control system 500 is configured to control or otherwise regulate a physiological condition in the body 501 of a user to a desired (or target) value or otherwise maintain the condition within a range of acceptable values. In one or more exemplary embodiments, the condition being regulated is sensed, detected, measured or otherwise quantified by a sensing arrangement 504 (e.g., sensing arrangement 104) communicatively coupled to the infusion device 502. However, it should be noted that in alternative embodiments, the condition being regulated by the control system 500 may be correlative to the measured values obtained by the sensing arrangement 504. That said, for clarity and purposes of explanation, the subject matter may be described herein in the context of the sensing arrangement 504 being realized as a glucose sensing arrangement that senses, detects, measures or otherwise quantifies the user's glucose level, which is being regulated in the body 501 of the user by the control system 500.

In exemplary embodiments, the sensing arrangement 504 includes one or more interstitial glucose sensing elements that generate or otherwise output electrical signals having a signal characteristic that is correlative to, influenced by, or otherwise indicative of the relative interstitial fluid glucose level in the body 501 of the user. The output electrical signals are filtered or otherwise processed to obtain a measurement value indicative of the user's interstitial fluid glucose level. In exemplary embodiments, a blood glucose meter 530, such as a finger stick device, is utilized to directly sense, detect, measure or otherwise quantify the blood glucose in the body 501 of the user. In this regard, the blood glucose meter 530 outputs or otherwise provides a measured blood glucose value that may be utilized as a reference measurement for calibrating the sensing arrangement 504 and converting a measurement value indicative of the user's interstitial fluid glucose level into a corresponding calibrated blood glucose value. For purposes of explanation, the calibrated blood glucose value calculated based on the electrical signals output by the sensing element(s) of the sensing arrangement 504 may alternatively be referred to herein as the sensor glucose value, the sensed glucose value, or variants thereof.

In the illustrated embodiment, the pump control system 520 generally represents the electronics and other components of the infusion device 502 that control operation of the fluid infusion device 502 according to a desired infusion delivery program in a manner that is influenced by the sensed glucose value indicative of a current glucose level in the body 501 of the user. For example, to support closed-loop control, the pump control system 520 maintains, receives, or otherwise obtains a target or commanded glucose value, and generates or otherwise determines dosage commands for operating the motor 507 to displace the plunger 517 and deliver insulin to the body 501 of the user based on the difference between a sensed value and the target value. In other operating modes, the pump control system 520 may generate or otherwise determine dosage commands configured to maintain the sensed glucose value below an upper glucose limit, above a lower glucose limit, or otherwise within a desired range of glucose values. In practice, the infusion device 502 may store or otherwise maintain the target value, upper and/or lower glucose limit(s), and/or other glucose threshold value(s) in a data storage element accessible to the pump control system 520. The target value and other threshold values may be received from an external component (e.g., CCD 106 and/or computing device 108) or be input by a user via a user interface element 540 associated with the infusion device 502. In practice, the one or more user interface element(s) 540 associated with the infusion device 502 typically include at least one input user interface element, such as, for example, a button, a keypad, a keyboard, a knob, a joystick, a mouse, a touch panel, a touchscreen, a microphone or another audio input device, and/or the like. Additionally, the one or more user interface element(s) 540 include at least one output user interface element, such as, for example, a display element (e.g., a light-emitting diode or the like), a display device (e.g., a liquid crystal display or the like), a speaker or another audio output device, a haptic feedback device, or the like, for providing notifications or other information to the user. It should be noted that although FIG. 5 depicts the user interface element(s) 540 as being separate from the infusion device 502, in practice, one or more of the user interface element(s) 540 may be integrated with the infusion device 502. Furthermore, in some embodiments, one or more user interface element(s) 540 are integrated with the sensing arrangement 504 in addition to and/or in alternative to the user interface element(s) 540 integrated with the infusion device 502. The user interface element(s) 540 may be manipulated by the user to operate the infusion device 502 to deliver correction boluses, adjust target and/or threshold values, modify the delivery control scheme or operating mode, and the like, as desired.

As described in greater detail below in the context of FIGS. 7-11, in exemplary embodiments, the pump control system 520 also includes or otherwise accesses a data storage element, memory, or other non-transitory computer-readable medium capable of storing programming instructions for execution by the pump control system 520. The computer-executable programming instructions, when read and executed, cause the pump control system 520 to determine values for one or more homeostasis metrics for the user, automatically provide alerts in a manner that is influenced by the values for the one or more homeostasis metrics, and perform the additional tasks, operations, functions, and processes described herein.

Still referring to FIG. 5, in the illustrated embodiment, the infusion device 502 includes a motor control module 512 coupled to a motor 507 (e.g., motor assembly 207) that is operable to displace a plunger 517 (e.g., plunger 217) in a reservoir (e.g., reservoir 205) and provide a desired amount of fluid to the body 501 of a user. In this regard, displacement of the plunger 517 results in the delivery of a fluid that is capable of influencing the condition in the body 501 of the user to the body 501 of the user via a fluid delivery path (e.g., via tubing 221 of an infusion set 225). A motor driver module 514 is coupled between an energy source 503 and the motor 507. The motor control module 512 is coupled to the motor driver module 514, and the motor control module 512 generates or otherwise provides command signals that operate the motor driver module 514 to provide current (or power) from the energy source 503 to the motor 507 to displace the plunger 517 in response to receiving, from a pump control system 520, a dosage command indicative of the desired amount of fluid to be delivered.

In exemplary embodiments, the energy source 503 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 503 into alternating electrical signals applied to respective phases of the stator windings of the motor 507 that result in current flowing through the stator windings that generates a stator magnetic field and causes the rotor of the motor 507 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 507 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 507 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 507 to achieve the desired delivery of fluid to the user.

When the motor control module 512 is operating the motor driver module 514, current flows from the energy source 503 through the stator windings of the motor 507 to produce a stator magnetic field that interacts with the rotor magnetic field. In some embodiments, after the motor control module 512 operates the motor driver module 514 and/or motor 507 to achieve the commanded dosage, the motor control module 512 ceases operating the motor driver module 514 and/or motor 507 until a subsequent dosage command is received. In this regard, the motor driver module 514 and the motor 507 enter an idle state during which the motor driver module 514 effectively disconnects or isolates the stator windings of the motor 507 from the energy source 503. In other words, current does not flow from the energy source 503 through the stator windings of the motor 507 when the motor 507 is idle, and thus, the motor 507 does not consume power from the energy source 503 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the motor control module 512, or in any practical combination thereof. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform the tasks, operations, functions, and processes described herein.

It should be appreciated that FIG. 5 is a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in practice, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 200, 400, while in alternative embodiments, the pump control system 520 may be implemented by a remote computing device that is physically distinct and/or separate from the infusion device 502, such as, for example, the CCD 106 or the computing device 108.

Figure 6:
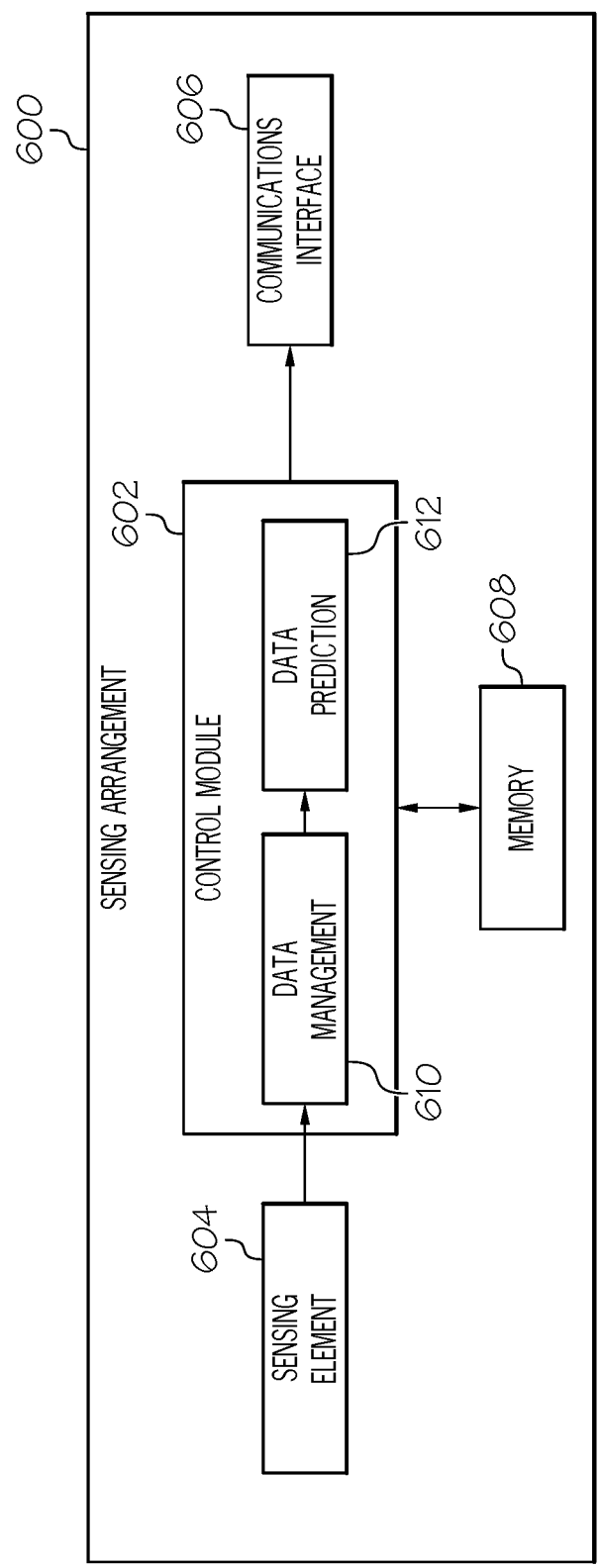
FIG. 6 is a block diagram of an exemplary sensing arrangement suitable for use in the control system of FIG. 5.

FIG. 6 depicts an exemplary embodiment of a sensing arrangement 600 suitable for use as the sensing arrangement 504 in FIG. 5 in accordance with one or more embodiments. The illustrated sensing arrangement 600 includes, without limitation, a control module 602, a sensing element 604, a communications interface 606, and a data storage element (or memory) 608. The control module 602 is coupled to the sensing element 604, the communications interface 606, and the memory 608, and the control module 602 is suitably configured to support the operations, tasks, and/or processes described herein.

The sensing element 604 generally represents the component of the sensing arrangement 600 that is configured to generate, produce, or otherwise output one or more electrical signals indicative of a characteristic that is sensed, measured, or otherwise quantified by the sensing arrangement. In this regard, a characteristic of the output electrical signal provided by the sensing element 604 corresponds or is otherwise correlative to the characteristic that the sensing element 604 senses, detects, measures, or otherwise quantifies. For example, referring to FIG. 5, the sensing element 604 may be realized as an interstitial glucose sensing element that generates an electrical signal, wherein a current, voltage, or other characteristic of the electrical signal is correlative to the interstitial fluid glucose level that is sensed or otherwise measured in the body 501 of the user.

Still referring to FIG. 6, the control module 602 generally represents the hardware, circuitry, logic, firmware and/or other component of the sensing arrangement 600 that is coupled to the sensing element 604 and configured to receive the measurement data from the sensing element 604 and perform various additional tasks, operations, functions and/or operations described herein. For example, in one or more embodiments, the control module 602 implements or otherwise executes a data management application 610 that processes the measurement data received from the sensing element 604 to detect or otherwise identify whether measurement data value received from the sensing element 604 is valid or otherwise acceptable, and when a measurement data value is unacceptable, the data management application 610 substitutes a modified measurement data value for the unacceptable measurement data value in a data sequence of the most recent measurement data values. Additionally, in one or more embodiments, the control module 602 also implements or otherwise executes a data prediction application 612 that calculates or otherwise determines one or more predicted values for the characteristic sensed by the sensing element 604 based on the sequence of the most recent measurement data values received from the data management application 610. In this regard, a predicted value for the sensed characteristic at a time in the future may be influenced by or otherwise based at least in part on the modified measurement data value substituted by the data management application 610 in lieu of the unacceptable measurement data value received from the sensing element 604, as described in greater detail below. In one or more exemplary embodiments, the sensing arrangement 504, 600 outputs or otherwise provides, to the pump control system 520, the measurement data value from the data management application 610 indicative of the current state of the user's physiological condition along with the predicted value(s) for the future state of the user's physiological condition determined by the data prediction application 612.

Depending on the embodiment, the control module 602 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the control module 602, or in any practical combination thereof. In some embodiments, the control module 602 includes an analog-to-digital converter (ADC) or another similar sampling arrangement that converts the output data signal received from the sensing element 604 into corresponding digital measurement data value. For example, the control module 602 may convert an output electrical signal received from the sensing element 604 into corresponding digital measurement value (e.g., an uncalibrated glucose sensor electrical current value).

In exemplary embodiments, the control module 602 includes or otherwise accesses the data storage element or memory 608. The memory 608 may be realized using any sort of RAM, ROM, flash memory, registers, hard disks, removable disks, magnetic or optical mass storage, short or long term storage media, or any other non-transitory computer-readable medium capable of storing programming instructions for execution by the control module 602. The computer-executable programming instructions, when read and executed by the control module 602, cause the control module 602 to implement or otherwise generate the applications 610, 612 and perform or otherwise support the tasks, operations, functions, and processes described in greater detail below.

The communications interface 606 generally represents the hardware, circuitry, logic, firmware and/or other components of the sensing arrangement 600 that are coupled to the control module 602 and configured to support communications to/from the sensing arrangement 600. The communications interface 606 may include or otherwise be coupled to one or more transceiver modules capable of supporting wireless communications between the sensing arrangement 600 and another electronic device (e.g., an infusion device 102, 200, 502 or another electronic device 106, 108 in an infusion system 100). Alternatively, the communications interface 606 may be realized as a port that is adapted to receive or otherwise be coupled to a wireless adapter that includes one or more transceiver modules and/or other components that support the operations of the sensing arrangement 600 described herein. In other embodiments, the communications interface 606 may be configured to support wired communications to/from the sensing arrangement 600.

It should be understood that FIG. 6 is a simplified representation of a sensing arrangement 600 for purposes of explanation and is not intended to limit the subject matter described herein in any way. In this regard, although FIG. 6 depicts the various elements residing within the sensing arrangement 600, one or more elements of the sensing arrangement 600 may be distinct or otherwise separate from the other elements of the sensing arrangement 600. For example, the sensing element 604 may be separate and/or physically distinct from the control module 602 and/or the communications interface 606. Furthermore, although FIG. 6 depicts the data management application 610 and the data prediction application 612 as being implemented by the sensing arrangement 600, in alternative embodiments, features and/or functionality of the data management application 610 and/or the data prediction application 612 may be implemented by or otherwise reside on the infusion device 102, 502 or another device 106, 108 within an infusion system 100.

Figure 7:
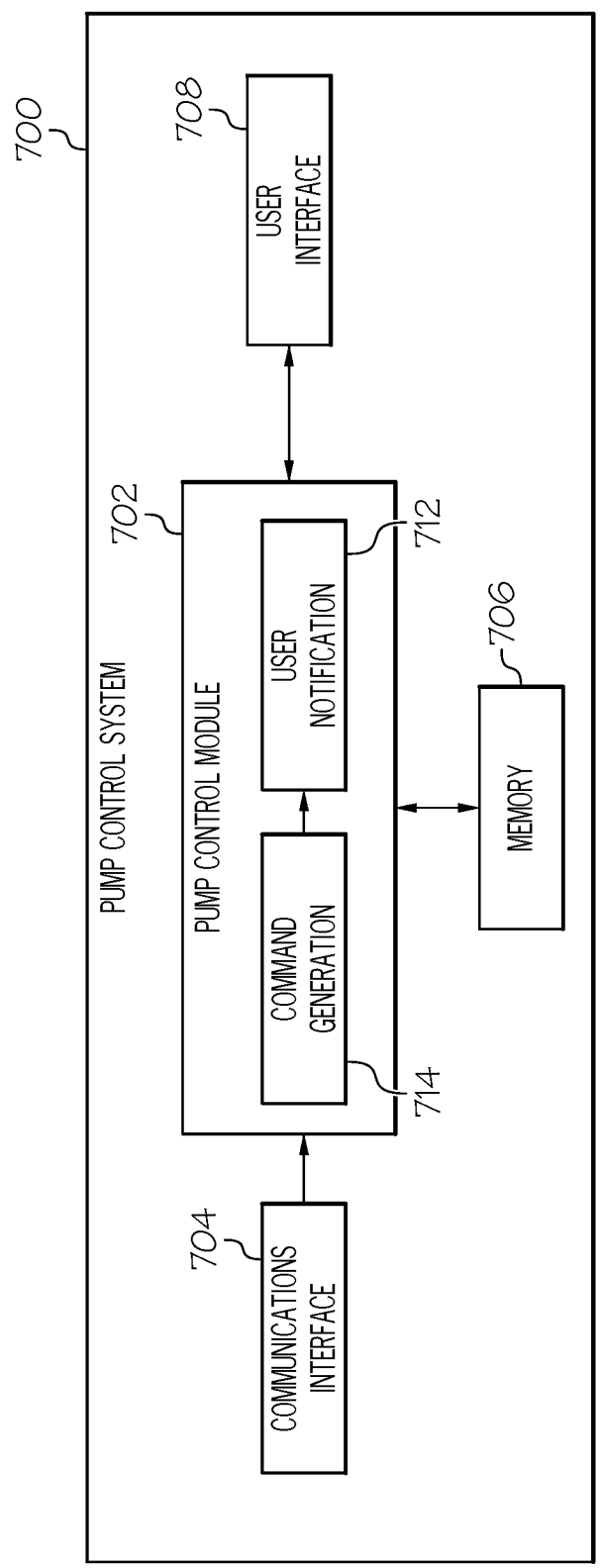
FIG. 7 is a block diagram of an exemplary pump control system suitable for use in the control system of FIG. 5.

FIG. 7 depicts an exemplary embodiment of a pump control system 700 suitable for use as the pump control system 520 in FIG. 5 in accordance with one or more embodiments. The illustrated pump control system 700 includes, without limitation, a pump control module 702, a communications interface 704, and a data storage element (or memory) 706. The pump control module 702 is coupled to the communications interface 704 and the memory 706, and the pump control module 702 is suitably configured to support the operations, tasks, and/or processes described herein. In exemplary embodiments, the pump control module 702 is also coupled to one or more user interface elements 708 (e.g., user interface 230, 540) for receiving bolus or other delivery instructions and providing notifications or other information to the user. Although FIG. 7 depicts the user interface element 708 as being integrated with the pump control system 700 (e.g., as part of the infusion device 200, 502), in various alternative embodiments, the user interface element 708 may be integrated with the sensing arrangement 504, 600 or another element of an infusion system 100 (e.g., the computer 108 or CCD 106).

Referring to FIG. 7 and with reference to FIG. 5, the communications interface 704 generally represents the hardware, circuitry, logic, firmware and/or other components of the pump control system 700 that are coupled to the pump control module 702 and configured to support communications between the pump control system 700 and the sensing arrangement 504. In this regard, the communications interface 704 may include or otherwise be coupled to one or more transceiver modules capable of supporting wireless communications between the pump control system 520, 700 and the sensing arrangement 504 or another electronic device 106, 108 in an infusion system 100. In other embodiments, the communications interface 704 may be configured to support wired communications to/from the sensing arrangement 504.

The pump control module 702 generally represents the hardware, circuitry, logic, firmware and/or other component of the pump control system 700 that is coupled to the communications interface 704 and configured to determine dosage commands for operating the motor 507 to deliver fluid to the body 501 based on data received from the sensing arrangement 504 and perform various additional tasks, operations, functions and/or operations described herein. For example, in exemplary embodiments, pump control module 702 implements or otherwise executes a command generation application 714 that calculates or otherwise determines a dosage command for operating the motor 507 of the infusion device 502 based at least in part on a current measurement value for a condition in the body 501 of the user. For example, the command generation application 714 may determine a dosage command for operating the motor 507 to deliver insulin to the body 501 of the user based at least in part on a current blood glucose measurement value, a predicted blood glucose measurement value at a time in the future (e.g., in 30 minutes from the current time), and a reference glucose value. In such embodiments, the reference value may be equal to the threshold blood glucose value at which insulin delivery should be suspended, wherein the command generation application 714 sets the dosage command to zero to suspend operation of the motor 507 (and thereby, suspend delivery) when the current blood glucose measurement value is less than or equal to the threshold blood glucose value. Conversely, when the current blood glucose measurement value is greater than a threshold blood glucose value (e.g., a resume delivery threshold), the command generation application 714 may determine a nonzero dosage command for operating the motor 507 to deliver insulin to the body 501 of the user based at least in part on the current blood glucose measurement value. In the case of closed-loop control, the dosage command determined by the command generation application 714 may be configured to regulate the user's blood glucose level to a target blood glucose value. Additionally, the command generation application 714 may generate dosage commands for boluses that are manually-initiated or otherwise instructed by a user via a user interface element 708.

In exemplary embodiments, pump control module 702 also implements or otherwise executes a notification application 712 that generates or otherwise provides user notifications or alerts via a user interface element 708 based at least in part on a current measurement value for a condition in the body 501 of the user (e.g., the current sensor glucose measurement value received from the sensing arrangement 504, 600). As described in greater detail below in the context of FIGS. 8-11, in exemplary embodiments, the notification application 712 calculates or otherwise determines values for one or more homeostasis metrics based at least in part on the sensor glucose measurement values received from the sensing arrangement 504, 600 and the dosage commands generated by the command generation application 714 and automatically generates user notifications in a manner that is influenced by the value of one or more of the homeostasis metrics.

Still referring to FIG. 7, depending on the embodiment, the control module 702 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the control module 702, or in any practical combination thereof. In exemplary embodiments, the pump control module 702 includes or otherwise accesses the data storage element or memory 706, which may be realized using any sort of non-transitory computer-readable medium capable of storing programming instructions for execution by the pump control module 702. The computer-executable programming instructions, when read and executed by the control module 702, cause the control module 702 to implement or otherwise generate one or more of the applications 712, 714 and perform the tasks, operations, functions, and processes described in greater detail below.

It should be understood that FIG. 7 is a simplified representation of a pump control system 700 for purposes of explanation and is not intended to limit the subject matter described herein in any way. For example, in some embodiments, the features and/or functionality of the motor control module 512 may be implemented by or otherwise integrated into the pump control system 700 and/or the pump control module 702, for example, by the command generation application 714 converting the dosage command into a corresponding motor command, in which case, the separate motor control module 512 may be absent from an embodiment of the infusion device 502.

Figure 8:
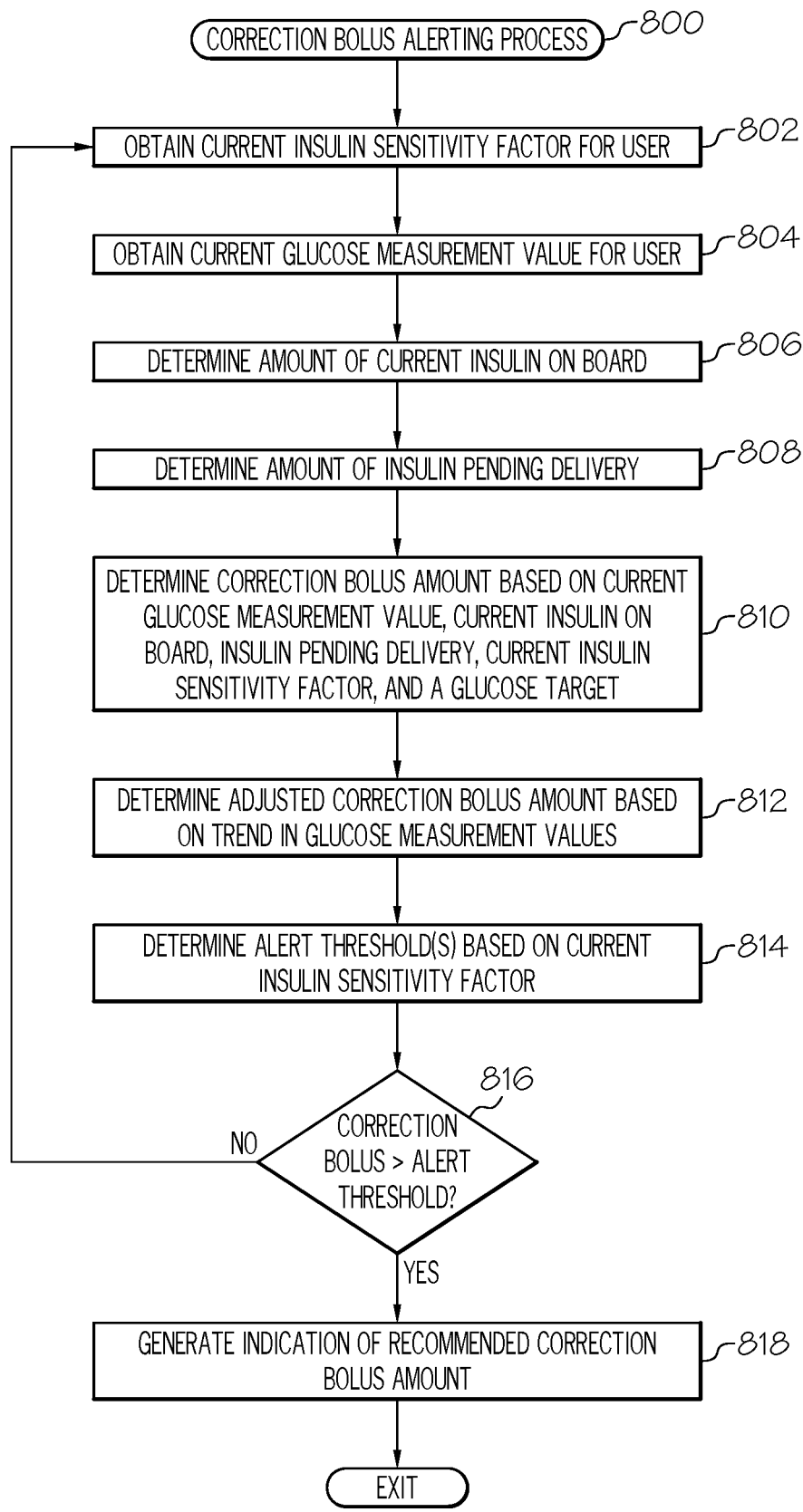
FIG. 8 is a flow diagram of an exemplary correction bolus alerting process suitable for use with the control system of FIG. 5.

FIG. 8 depicts an exemplary correction bolus alerting process 800 suitable for implementation by a control system associated with a fluid infusion device, such as the control system 500 in the infusion device 502, to notify the user that he or she may need an additional correction bolus based on the relationship between a user's current measurement value, the current amount of active fluid in the body of the user, and any anticipated or scheduled fluid deliveries. The various tasks performed in connection with the correction bolus alerting process 800 may be performed by hardware, firmware, software executed by processing circuitry, or any combination thereof. For illustrative purposes, the following description refers to elements mentioned above in connection with FIGS. 1-7. In practice, portions of the correction bolus alerting process 800 may be performed by different elements of the control system 500, such as, for example, the infusion device 502, the sensing arrangement 504, 600, the pump control system 520, 700, the notification application 712, the command generation application 714, and/or the user interface 540, 708. It should be appreciated that the correction bolus alerting process 800 may include any number of additional or alternative tasks, the tasks need not be performed in the illustrated order and/or the tasks may be performed concurrently, and/or the correction bolus alerting process 800 may be incorporated into a more comprehensive procedure or process having additional functionality not described in detail herein. Moreover, one or more of the tasks shown and described in the context of FIG. 8 could be omitted from a practical embodiment of the correction bolus alerting process 800 as long as the intended overall functionality remains intact.

In the illustrated embodiment, the correction bolus alerting process 800 initializes or otherwise begins by obtaining a current insulin sensitivity factor for the user (task 802). In some embodiments, the current insulin sensitivity factor is set by the user, and the user may manually adjust the insulin sensitivity factor to reflect physiological changes that are influenced by the time of day. In other embodiments, the current insulin sensitivity factor may be calculated or otherwise determined by the pump control system 520, 700. In such embodiments, the pump control system 520, 700 may store or otherwise maintain historical insulin delivery information for the user based on dosage commands previously provided to the motor control module 512 and calculate or otherwise determine the user's current insulin sensitivity factor based on the amount of insulin delivered to the user over a preceding time interval. For example, the pump control system 520, 700 may dynamically calculate the current insulin sensitivity factor for the user based on the amount of insulin delivered during the preceding 24-hour period.

The correction bolus alerting process 800 also receives or otherwise obtains a current glucose measurement value for the user (task 804). For example, the pump control system 520, 700 may periodically receive or otherwise obtain a new (or updated) interstitial fluid glucose measurement value from the sensing arrangement 504, 600. In exemplary embodiments, the measurement value most recently received from the sensing arrangement 504, 600 is treated as the current measurement of the user's glucose level. In this regard, the correction bolus alerting process 800 may be performed in response to each new measurement value received from the sensing arrangement 504, 600.

In exemplary embodiments, the correction bolus alerting process 800 obtains, identifies, or otherwise determines a current amount of insulin on board in the body of the user (task 806). In one or more embodiments, the notification application 712 calculates or otherwise determines the user's current IOB based on any insulin that has previously been delivered (e.g., the insulin automatically delivered as a result of the delivery control scheme implemented by the command generation application 714 and any manually-initiated boluses of insulin) using the appropriate pharmacokinetics/pharmacodynamics model corresponding to the user's insulin response (e.g., using time constants corresponding to the user's insulin response) to account for the insulin that has already been metabolized or is no longer active. In other embodiments, the current IOB may be calculated by the command generation application 714 or elsewhere within the control system 500 and/or the pump control system 520, 700 and obtained therefrom by the notification application 712. Depending on the embodiment, the current IOB may be calculated as the current IOB in the subcutaneous compartment, the current IOB in the plasma compartment plus the current IOB in the subcutaneous compartment, or the current IOB in the effect site compartment plus the current IOB in both the plasma compartment and the subcutaneous compartment.

It should be appreciated that there a numerous different techniques for determining the current IOB, and the subject matter described herein is not limited to any particular manner of estimating, calculating, or otherwise determining the user's current IOB. In some embodiments, the current IOB for the user may be estimated using a lookup table that has been populated with experimental data for various combinations of deliveries and various timings thereof. In other embodiments, the current IOB for the user may be determined on a substantially continuous basis and substantially in real-time based on all insulin delivered. For example, assuming an infusion rate $u_a(t)$ in units per hour (U/h), a pharmacokinetic model for the subcutaneous infusion of insulin is given by the following ordinary differential equations:

$$\dot{I}_S(t) = -\frac{1}{\tau_1} I_S(t) + \frac{1}{\tau_1} u_a(t),$$

$$\dot{I}_P(t) = -\frac{1}{\tau_2} I_P(t) + \frac{1}{\tau_2} I_S(t), \text{ and}$$

$$\dot{I}_E(t) = -\frac{1}{\tau_3} I_E(t) + \frac{1}{\tau_3} I_P(t),$$

where $I_S(t)$ corresponds to the subcutaneous compartment, $I_P(t)$ corresponds to the subcutaneous plus plasma compartment, $I_E(t)$ corresponds to the effect site compartment, $u_a(t)$ includes or otherwise accounts for both basal and bolus infusions, and the $\tau_n$ terms are the respective time constants associated therewith. For example, for a rapid-acting insulin such as as part, $\tau_1=50/60$ h, $\tau_2=70/60$ h, and $\tau_3=55/60$ h.

The total insulin on board can be calculated using one or more of the compartments using equations:

$$IOB_1(t) = \int_0^t U_a(\tau)d\tau - \int_0^t I_S(\tau)d\tau,$$

$$IOB_2(t) = \int_0^t U_a(\tau)d\tau - \int_0^t I_P(\tau)d\tau, \text{ and}$$

$$IOB_3(t) = \int_0^t U_a(\tau)d\tau - \int_0^t I_E(\tau)d\tau,$$

where $IOB_1(t)$ corresponds to the insulin on board in the subcutaneous compartment, $IOB_2(t)$ corresponds to the insulin on board in the plasma compartment, and $IOB_3(t)$ corresponds to the insulin on board in all three compartments. These equations can be rewritten in the Laplace domain as:

$$IOB_1(s) = \frac{\tau_1}{(\tau_1 s + 1)} U_a(s),$$

$$IOB_2(s) = \frac{\tau_1 \tau_2 s + \tau_1 + \tau_2}{(\tau_1 s + 1)(\tau_2 s + 1)} U_a(s), \text{ and}$$

$$IOB_3(s) = \frac{\tau_1 \tau_2 \tau_3 s^2 + (\tau_1 \tau_2 + \tau_1 \tau_3 + \tau_2 \tau_3)s + \tau_1 + \tau_2 + \tau_3}{(\tau_1 s + 1)(\tau_2 s + 1)(\tau_3 s + 1)} U_a(s).$$

Still referring to FIG. 8, in exemplary embodiments, the correction bolus alerting process 800 also identifies or otherwise determines the amount of any pending, scheduled, or otherwise anticipated insulin deliveries in the future (task 808). In this regard, the notification application 712 obtains, from the command generation application 714, delivery information pertaining to pending delivery commands that have already been generated and/or scheduled by the command generation application 714 for implementation by the motor control module 512 at some point in the future. For example, the pump control system 520, 700 and/or command generation application 714 may be instructed or otherwise configured to implement a bolus with an extended delivery time (e.g., a square wave bolus). The pending delivery information may include, for example, the scheduled timing of subsequent delivery commands and the respective amounts of insulin to be delivered by the respective delivery commands.

The correction bolus alerting process 800 continues by calculating or otherwise determining an estimated correction bolus amount for maintaining the user's glucose level at a target glucose value based on the relationship between the user's current glucose measurement value, the user's current IOB, and the anticipated future insulin deliveries (task 810). In exemplary embodiments, the notification application 712 determines a difference between the most recent interstitial fluid glucose measurement value and a target glucose value, converts the difference to an amount of insulin using the user's current insulin sensitivity factor, and subtracts the sum of the user's current IOB and the amount of future insulin deliveries from that amount to obtain a correction bolus amount for regulating the user's glucose level to the target value. For example, the correction bolus amount ($I_B$) for regulating the user's glucose level to the target value may be governed by the equation $$I_B = \max\left(\frac{G_S - G_T}{I_{SF}} - I_{OB} - I_{PD}, 0\right),$$

where $G_S$ is the interstitial fluid glucose measurement value most recently obtained from the sensing arrangement 504, 600, $G_T$ is the target glucose value, $I_{SF}$ is the user's current insulin sensitivity factor, $I_{OB}$ is the user's current IOB (e.g., the current IOB in the effect site compartment plus the current IOB in both the plasma compartment and the subcutaneous compartment), and $I_{PD}$ is the total amount of insulin pending delivery. In one embodiment, the target glucose value may be realized as a glucose setpoint utilized by a closed-loop control mode implemented by the pump control system 520, 700. In other embodiments, the target glucose value may be a hyperglycemic threshold value or some other upper glucose limit that the user does not want to exceed.

In exemplary embodiments, the correction bolus alerting process 800 continues by adjusting the correction bolus amount based on the current trend in the user's current glucose measurement values (task 812). In this regard, because interstitial fluid glucose measurement values are not as accurate as blood glucose measurement values that would otherwise be obtained via the blood glucose meter 530, incorporating trend information reduces the probability of issuing a non-actionable alert (and conversely, increases the likelihood that the generated alerts will be actionable). For example, the adjusted correction bolus amount ($I_{BC}$) may be determined by multiplying the estimated correction bolus amount by a factor that is correlative to the derivative (or rate of change) of the user's recent glucose measurement values (e.g., $I_{BC} = T_{ADJ} \times I_B$). In such embodiments, the adjustment factor is greater than one when the difference between the user's current glucose measurement value and the preceding glucose measurement value indicates an upward trend in the user's current glucose measurement values and less than one when the difference between the user's current glucose measurement value and the preceding glucose measurement value indicates a downward trend in the user's current glucose measurement values. For example, in one embodiment, the notification application 712 determines the difference between the user's current glucose measurement value and the preceding glucose measurement value and sets the trend adjustment factor ($T_{ADJ}$) to a value of 1.2 when the difference is greater than or equal to 2 mg/dL/min, a value of 1.1 when the difference is greater than or equal to 1 mg/dL/min but less than 2 mg/dL/min, a value of 0 when the difference is less than or equal to −1 mg/dL/min, and otherwise sets the trend adjustment factor to a value of 1 when the difference is between −1 mg/dL/min and 1 mg/dL/min. It should be appreciated that there are numerous possible ways in which the trend adjustment factor may be determined, and the subject matter described herein is not intended to be limited to any particular manner of determining the trend adjustment factor.

The illustrated correction bolus alerting process 800 continues by calculating or otherwise determining an alert threshold for notifying the user when additional insulin may be required based the estimated correction bolus amount (task 814). In exemplary embodiments, the alert threshold value is determined based at least in part on the user's current insulin sensitivity factor. In this regard, the alert threshold may be dynamically adjusted or updated for each iteration of the correction bolus alerting process 800 to account for changes in the user's insulin sensitivity. For example, the alert threshold value ($I_{Bth}$) may be determined by the notification application 712 using the equation $$I_{Bth} = \frac{G_D}{I_{SF}},$$

where $I_{SF}$ is the user's current insulin sensitivity factor and $G_D$ represents the tolerable difference between an upper glucose threshold value and the glucose target value ($G_T$) (or alternatively, the tolerable deviation from the glucose target value). The upper glucose threshold value and/or the tolerable deviation from the glucose target value ($G_T$) may be manually configured by the user via the user interface 540, 708 or may be selected or otherwise identified from a list of possible alert settings. For example, the user may select from a smaller tolerable deviation for more frequent alerts (e.g., $G_D$=25 mg/dL), a larger tolerable deviation for less frequent alerts (e.g., $G_D$=75 mg/dL), or an intermediate or nominal alert setting (e.g., $G_D$=50 mg/dL). In embodiments where the glucose target value is a hyperglycemic threshold, the tolerable deviation may be set to zero (e.g., $G_D$=0), such that an alert is generated whenever the estimated correction bolus amount is greater than zero. In some embodiments, the tolerable difference may have different values for different times of day, for example, in the event that the user wants more or less frequent alerts during a particular time of day.

The correction bolus alerting process 800 continues by identifying or otherwise determining whether the estimated correction bolus amount is greater than the alert threshold and generating or otherwise providing an alert when the estimated correction bolus amount is greater than the alert threshold (tasks 816, 818). In this regard, when the estimated correction bolus amount is greater than the alert threshold (e.g., $I_{BC}$>$I_{Bth}$), the pump control system 520, 700 and/or the notification application 712 automatically generates or otherwise provides an indication to the user via the user interface 540, 708 that notifies the user that additional insulin may be required. In exemplary embodiments, the pump control system 520, 700 and/or the notification application 712 generates a user notification that provides an indication of a recommended amount of additional insulin that may be required. For example, the pump control system 520, 700 and/or the notification application 712 may cause the user interface 540, 708 to display the estimated correction bolus amount ($I_{BC}$) as a recommended correction bolus to the user. In response, the user responding to the alert may manipulate the user interface 540, 708 to clear the alert and instruct, signal, or otherwise command the command generation application 714 to implement the recommended correction bolus or a different amount as desired by the user. In one or more alternative embodiments, the notification application 712 may automatically instruct, signal, or otherwise command the command generation application 714 to initiate implementing the recommended correction bolus concurrently to generating an alert indicating the recommend correction bolus (or in some embodiments, in lieu of generating an alert).

Still referring to FIG. 8, when the estimated correction bolus amount is less than the alert threshold, the loop defined by tasks 802, 804, 806, 808, 810, 812, 814 and 816 may repeat throughout operation of the infusion device 102, 200, 502 to continuously monitor the relationship between the user's current glucose measurement value, current IOB, and pending insulin deliveries and identify when additional action may be required to prevent the user's glucose level from deviating from a target value by more than a tolerable amount. When the estimated correction bolus amount is less than the alert threshold, the notification application 712 determines that the user's glucose level is likely to be within a tolerable deviation from the target glucose level and does not generate any alerts. In such a situation, no affirmative action by the user is required to maintain the glucose level below the tolerable deviation from the target glucose level. Thus, even though a predicted glucose level for the user may exceed an upper glucose threshold value (or exceed the glucose target value by more than the threshold amount), the notification application 712 may determine that the user's glucose level is still likely to settle below the upper glucose threshold value based on the current IOB and anticipated insulin deliveries. Accordingly, the notification application 712 may suppress or otherwise disable any alerts that would otherwise be generated based on the predicted glucose level exceeding an upper glucose threshold value because they are unlikely to be actionable. By decreasing the number of non-actionable alerts that are generated, it is believed that the user experience will be improved and that users will be more likely to promptly address alerts that actually are generated due to the increased likelihood that they are actionable.

It should be noted that while many existing alerting strategies imply a trade-off between too many non-actionable alarms because of a low threshold to catch those cases when insulin is needed versus a higher threshold to minimize non-actionable alarms at the expense of degraded glycemic control (e.g., by virtue of generating alerts only after glucose values have become sufficiently elevated), the correction bolus alerting process 800 decouples these two objectives. For example, the correction bolus alerting process 800 may preemptively alert the user in situations where they might need a correction bolus (e.g., the user forgets to bolus for a meal or the user underestimated the carbohydrate content) before hyperglycemia is reached. A severe hyperglycemia alerting threshold can then be comfortably set at a relatively high threshold value (e.g., 300 mg/dL), which could trigger regardless of insulin on board and with a reduced likelihood of non-actionable hyperglycemic alerts.

Figure 9:
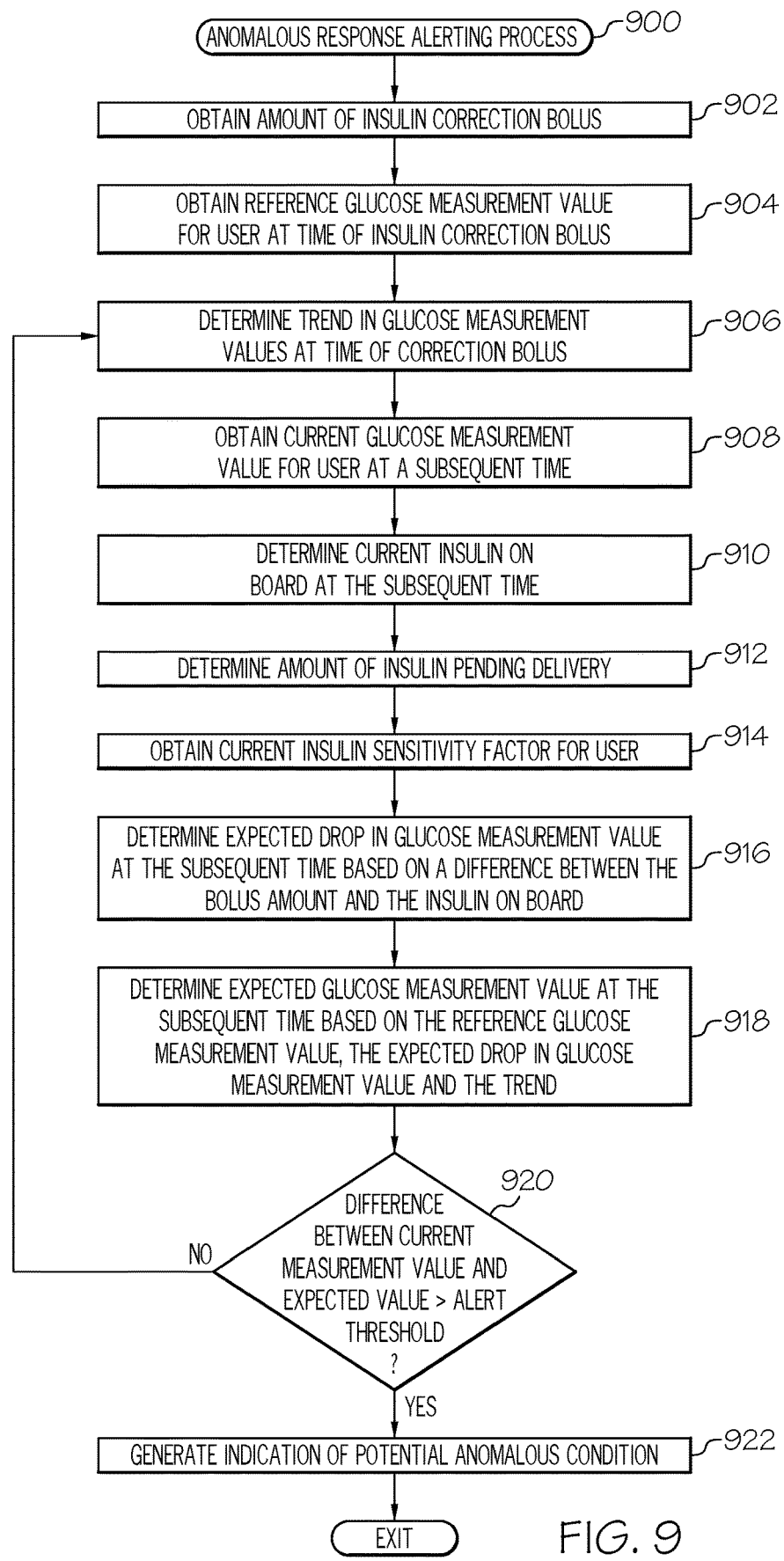
FIG. 9 is a flow diagram of an exemplary anomalous response alerting process suitable for use with the control system of FIG. 5.

FIG. 9 depicts an exemplary anomalous response alerting process 900 suitable for implementation by a control system associated with a fluid infusion device, such as the control system 500 in the infusion device 502, to notify the user of a potential anomalous condition when a previously-administered bolus is not exhibiting the anticipated effect. The various tasks performed in connection with the anomalous response alerting process 900 may be performed by hardware, firmware, software executed by processing circuitry, or any combination thereof. For illustrative purposes, the following description refers to elements mentioned above in connection with FIGS. 1-7. In practice, portions of the anomalous response alerting process 900 may be performed by different elements of the control system 500, such as, for example, the infusion device 502, the sensing arrangement 504, 600, the pump control system 520, 700, the notification application 712, the command generation application 714, and/or the user interface 540, 708. It should be appreciated that the anomalous response alerting process 900 may include any number of additional or alternative tasks, the tasks need not be performed in the illustrated order and/or the tasks may be performed concurrently, and/or the anomalous response alerting process 900 may be incorporated into a more comprehensive procedure or process having additional functionality not described in detail herein. Moreover, one or more of the tasks shown and described in the context of FIG. 9 could be omitted from a practical embodiment of the anomalous response alerting process 900 as long as the intended overall functionality remains intact.

The anomalous response alerting process 900 initializes or otherwise begins by receiving or otherwise obtaining a reference glucose measurement for the user at the time a correction bolus was administered along with an amount of insulin that was infused as part of the correction bolus (tasks 902, 904). In this regard, when the user manipulates the user interface element 708 to instruct, command or otherwise operate the pump control system 520, 700 and/or the command generation application 714 to implement a correction bolus, the notification application 712 may also receive or otherwise obtain a total amount of insulin delivered as part of the correction bolus. Additionally, in response to identifying the correction bolus, the notification application 712 receives or otherwise obtains the current glucose measurement value from the sensing arrangement 504, 600 at the time of the correction bolus for use as a reference glucose measurement value for the user at the time of the correction bolus. In one or more embodiments, when the current glucose measurement is not provided by the sensing arrangement 504, 600 simultaneous or contemporaneous to the delivery of the correction bolus, the notification application 712 may determine the reference glucose measurement value for the user at the time of the correction bolus by averaging the most recent glucose measurement value preceding the correction bolus delivery with the next glucose measurement value obtained after the correction bolus delivery. Alternatively, the notification application 712 may select the reference glucose measurement value as the glucose measurement value obtained closest in time to the time of the correction bolus. When the correction bolus is substantially contemporaneous to a blood glucose measurement value obtained via the blood glucose meter 530, the notification application 712 may select that blood glucose measurement value for use as the reference glucose measurement value.

In exemplary embodiments, the anomalous response alerting process 900 also calculates or otherwise determines a trend in the user's glucose measurement values at the time of the correction bolus (task 906). In this regard, the notification application 712 may obtain recent glucose measurement values that are stored or otherwise buffered by the pump control system 520, 700 (e.g., in memory 706) and determine the average rate of change among two or more glucose measurement values preceding the correction bolus. For example, the notification application 712 may determine the difference between two successive glucose measurement values preceding the correction bolus. In other embodiments, the notification application 712 may average the differences between all of the sets of successive glucose measurement values preceding the correction bolus that are stored in the memory 706. For example, in some embodiments, the glucose measurement values obtained over a preceding time interval (e.g., the preceding 40 minutes) may be stored or buffered in a first-in first-out manner. In some embodiments, the notification application 712 may calculate or otherwise estimate one or more predicted glucose measurement values (e.g., by implementing a Kalman filter or another forecasting or prediction algorithm), and calculate or otherwise determine the trend in the user's glucose measurement values in a manner that is influenced by the predicted glucose measurement values at the time of the correction bolus. In other words, predicted glucose measurement value(s) may be utilized to adjust or otherwise modify the trend determined based on the recent glucose measurement values preceding the correction bolus.

In the illustrated embodiment, the anomalous response alerting process 900 continues by receiving or otherwise obtaining a current glucose measurement value for the user at a subsequent time after the correction bolus delivery (task 908). In exemplary embodiments, the notification application 712 of the pump control system 520, 700 periodically receives a new (or updated) interstitial fluid glucose measurement value from the sensing arrangement 504, 600 in a similar manner as described above. Additionally, the anomalous response alerting process 900 also obtains, identifies, or otherwise determines the current amount of insulin on board in the body of the user at that subsequent time along with the amount of pending insulin deliveries at the subsequent time (tasks 910, 912). In a similar manner as described above, the notification application 712 calculates or otherwise determines the user's current IOB based on any insulin that has previously been delivered using the appropriate pharmacokinetics/pharmacodynamics model corresponding to the user's insulin response. Additionally, the notification application 712 obtains delivery information pertaining to pending delivery commands that have already been generated by the command generation application 714 for implementation by the motor control module 512 at some point in the future.

Still referring to FIG. 9, the illustrated process 900 continues by identifying or otherwise obtaining the current insulin sensitivity factor for the user, and calculating or otherwise determining an expected drop in the user's glucose measurement value at the subsequent time based on the amount of the correction bolus, the current IOB at the subsequent time, the pending insulin deliveries at the subsequent time, and the current insulin sensitivity factor (tasks 914, 916). The expected drop at the subsequent time ($G_d(t)$) may be determined using the equation $G_d(t)=I_{SF}(I_B-I_{OB}(t)-I_{PD}(t))$, where $I_{SF}$ is the user's current insulin sensitivity factor, $I_B$ is the correction bolus amount, $I_{OB}(t)$ is the user's current IOB at the subsequent time, and $I_{PD}(t)$ is the pending insulin deliveries at the subsequent time. The expected drop represents an acceptable or tolerable minimum observed response to the correction bolus based on the user's current insulin sensitivity factor that is compensated for the user's current IOB and pending insulin deliveries. In this regard, the expected drop accounts for the effect of the already processed (or metabolized) insulin from the correction bolus as time elapses (e.g., by incorporating the $I_{OB}(t)$ term).

In exemplary embodiments, the anomalous response alerting process 900 continues by calculating or otherwise determining an expected glucose measurement value at the subsequent time based on the reference glucose measurement value, the expected drop, and the trend in the user's glucose measurement values at the time of the correction bolus (task 918). The expected glucose measurement value at the subsequent time ($G_e(t)$) may be determined using the equation $G_e(t)=(G(t_B)+G_c(t_B))-G_d(t)$, where $G(t_B)$ is the reference glucose measurement value at the time of the correction bolus and $G_c(t_B)$ represents the compensation for the trend in the user's glucose measurement values at the time of the correction bolus. The expected glucose measurement value represents an acceptable or tolerable maximum glucose measurement value that is likely to be compensated for by the user's current IOB and pending insulin deliveries based on the user's current insulin sensitivity factor. It will be appreciated that the expected glucose measurement value also accounts for the effect of the already processed (or metabolized) insulin from the correction bolus as time elapses by way of the expected drop being influenced by the user's current IOB.

In response to identifying or otherwise determining that the user's current glucose measurement value at the subsequent time is greater than the expected glucose measurement value, the anomalous response alerting process 900 automatically generates or otherwise provides an alert indicative of a potential anomalous condition (task 920). In this regard, the difference or deviation between the user's current glucose measurement value at a particular time and the expected glucose measurement value at that time may be indicative of a potential anomaly in the fluid delivery path, a potential anomaly with the sensing arrangement 504, 600, that the amount of the correction bolus was incorrectly calculated based on the carbohydrates consumed by the user (or erroneously entered), or that the user is otherwise exhibiting an anomalous response to the correction bolus. In one embodiment, the notification application 712 determines a difference between the user's current glucose measurement value and the expected glucose measurement value, and identifies an alert condition when the difference is greater than a threshold value (e.g., a fixed percentage of the expected glucose measurement value at that particular time). In other embodiments, the notification application 712 calculates an upper confidence limit based on the expected glucose measurement value and identifies an alert condition when the user's current glucose measurement value is greater than the upper confidence limit value. When the anomalous response alerting process 900 identifies an alert condition based on the user's current glucose measurement value not exhibiting the expected response, the notification application 712 may generate or otherwise provide a graphical user notification on a display device 540, 708 that notifies or otherwise instructs the user to perform one or more remedial actions. For example, the notification application 712 may recommend inspecting the fluid delivery path, operating the blood glucose meter 530 to obtain a new reference blood glucose measurement value for recalibrating the sensing arrangement 504, 600, administering an additional correction bolus, or the like.

Still referring to FIG. 9, when the user's current glucose measurement value is less than the expected glucose measurement value (or within a threshold of the expected glucose measurement value), the loop defined by tasks 906, 908, 910, 912, 914, 916, 918 and 920 may repeat throughout operation of the infusion device 102, 200, 502 to continuously monitor the user's response to correction boluses and identify when the observed response deviates from the expected response. When the user's current glucose measurement value is less than the expected glucose measurement value, the notification application 712 determines that the insulin is having the desired or intended effect and does not generate any alerts because no affirmative action by the user is required to reduce the user's glucose level. In this regard, even though a predicted glucose level for the user may exceed an upper glucose threshold value (or exceed the glucose target value by more than the threshold amount), the notification application 712 determines the user's glucose level is exhibiting at least the minimum expected response to the correction bolus and that the user's glucose level is likely to settle below an upper glucose threshold value (assuming the correction bolus was configured to prevent a hyperglycemic event). Accordingly, the notification application 712 may suppress or otherwise disable any alerts that would otherwise be generated based on the predicted glucose level exceeding an upper glucose threshold value because they are unlikely to be actionable. Again, by decreasing the number of non-actionable alerts that are generated, it is believed that the user experience will be improved and that users will be more likely to promptly address alerts that actually are generated due to the increased likelihood that they are actionable.

At the same time, when the user's current glucose measurement value is greater than the expected glucose measurement value, the notification application 712 may generate an alert notifying the user that the glucose level is not exhibiting the desired or intended effect even though a predicted glucose level for the user may not exceed an upper glucose threshold value or the trend in the user's glucose level has reversed directions (e.g., the user's glucose level is starting to drop). Thus, the user may be notified of a potential anomaly in one or more of the fluid delivery path, the sensing arrangement 504, 600, the correction bolus calculation and/or entry, or the user's insulin response.

Figure 10:
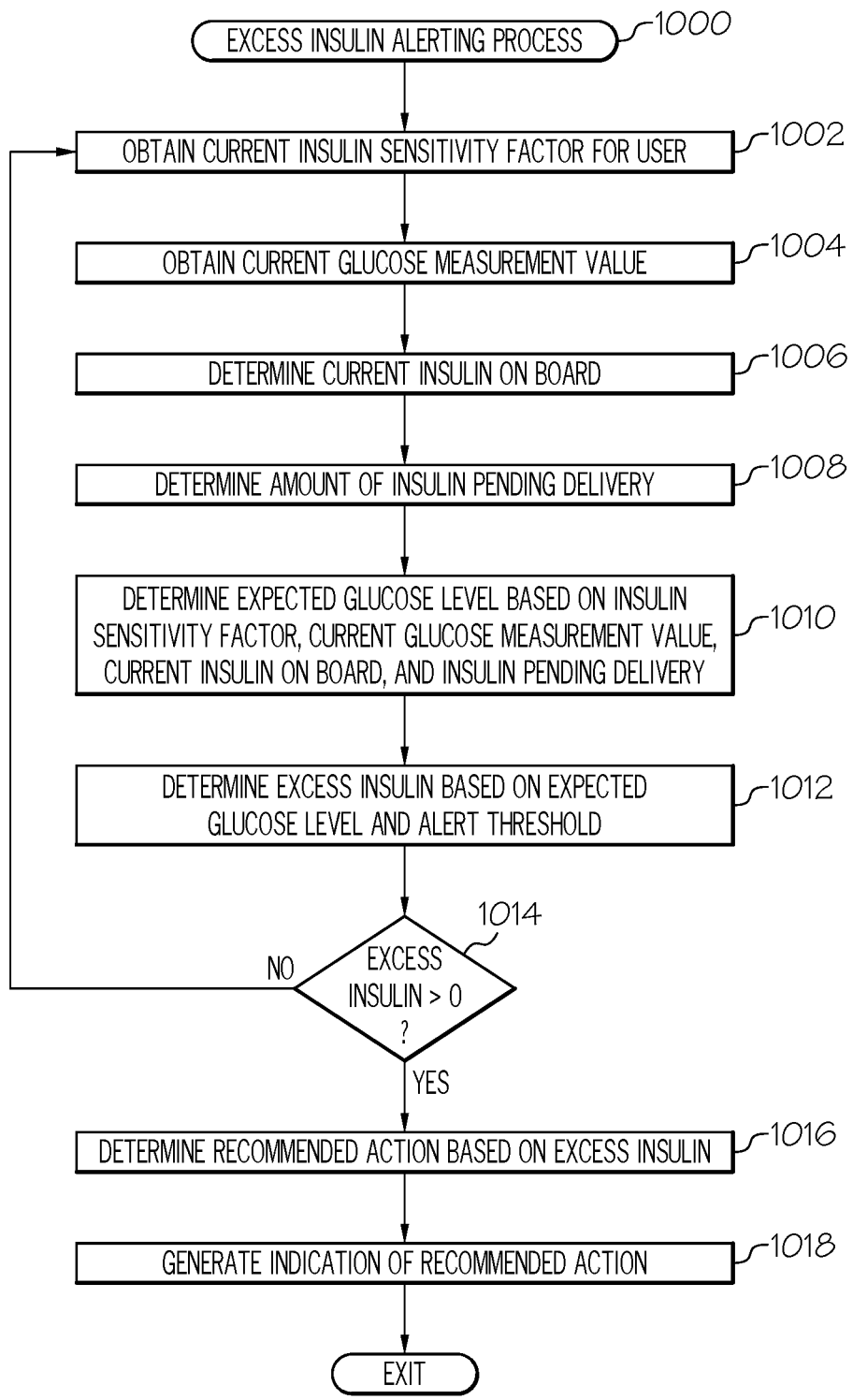
FIG. 10 is a flow diagram of an exemplary excess insulin alerting process suitable for use with the control system of FIG. 5.

FIG. 10 depicts an exemplary excess insulin alerting process 1000 suitable for implementation by a control system associated with a fluid infusion device, such as the control system 500 in the infusion device 502, to preemptively notify the user to consume additional carbohydrates or decrease (or disable) future insulin deliveries to mitigate or otherwise avoid an excess insulin condition. The various tasks performed in connection with the excess insulin alerting process 1000 may be performed by hardware, firmware, software executed by processing circuitry, or any combination thereof. For illustrative purposes, the following description refers to elements mentioned above in connection with FIGS. 1-7. In practice, portions of the excess insulin alerting process 1000 may be performed by different elements of the control system 500, such as, for example, the infusion device 502, the sensing arrangement 504, 600, the pump control system 520, 700, the notification application 712, the command generation application 714, and/or the user interface 540, 708. It should be appreciated that the excess insulin alerting process 1000 may include any number of additional or alternative tasks, the tasks need not be performed in the illustrated order and/or the tasks may be performed concurrently, and/or the excess insulin alerting process 1000 may be incorporated into a more comprehensive procedure or process having additional functionality not described in detail herein. Moreover, one or more of the tasks shown and described in the context of FIG. 10 could be omitted from a practical embodiment of the excess insulin alerting process 1000 as long as the intended overall functionality remains intact.

In a similar manner as described above in the context of FIG. 8, the excess insulin alerting process 1000 obtains a current insulin sensitivity factor for the user, a current glucose measurement value for the user, a current amount of insulin on board in the body of the user, and the amount of any pending insulin deliveries in the future (tasks 1002, 1004, 1006, 1008). Thereafter, the excess insulin alerting process 1000 calculates or otherwise determines an estimate of the user's glucose level after the insulin on board and the pending insulin deliveries are metabolized (task 1010). The notification application 712 calculates or otherwise determines an expected drop in the user's glucose measurement value based on the user's current IOB, the total amount of the pending insulin, and the user's current insulin sensitivity factor. The expected drop ($G_A$) may be determined using the equation $G_A = I_{SF}(I_{OB} + I_{PD})$, where $I_{SF}$ is the user's current insulin sensitivity factor, $I_{OB}$ is the user's current IOB, and $I_{PD}$ is the total amount of insulin pending delivery. Thereafter, the notification application 712 calculates or otherwise determines an expected glucose level ($G_E$) based on the expected drop and the user's current glucose measurement value using equation $G_E = G_S - G_A$, where $G_S$ is the user's current (or most recent) glucose measurement value obtained from the sensing arrangement 504, 600.

In the illustrated embodiment, the excess insulin alerting process 1000 calculates or otherwise determines an estimated amount of excess insulin based at least in part on the expected glucose level and an excess insulin alert threshold (task 1012). Depending on the embodiment, the excess alert threshold may be realized as the lowest acceptable glucose level (e.g., a hypoglycemia threshold), a delivery suspension threshold, or another glucose level at which the user would like to be notified to consume carbohydrates or otherwise perform one or more remedial actions. In this regard, the user may manipulate the user interface 540, 708 to interact with the notification application 712 and configure the excess insulin alert threshold as desired. The estimated amount of excess insulin ($I_E$) may be determined by converting the difference between the excess insulin alert threshold and the expected glucose level to an amount of insulin using the user's current insulin sensitivity factor. In exemplary embodiments, the estimated amount of excess insulin ($I_E$) is calculated using the equation $$I_E = \max\left(\frac{G_T - G_E}{I_{SF}}, 0\right),$$

where $G_T$ is the excess insulin alert threshold.

In response to determining the amount of excess insulin is greater than zero, the excess insulin alerting process 1000 identifies or otherwise determines a recommended remedial action based on the amount of excess insulin and generates or otherwise provides an alert that notifies the user of the potential excess insulin condition and the recommended remedial action (tasks 1014, 1016, 1018). For example, in one or more embodiments, the notification application 712 compares the estimated amount of excess insulin to the amount of insulin pending delivery and determines the recommended remedial action to be suspending one or more pending deliveries when the excess insulin is less than the amount of insulin pending delivery (e.g., when $0 < I_E \leq I_{PD}$). In this regard, the notification application 712 may identify commanded deliveries to be disabled or otherwise canceled to reduce the amount of insulin pending delivery by the amount of excess insulin, resulting in a recommended future insulin delivery ($I_R$) equal to the initial amount of insulin pending delivery minus the excess insulin ($I_R = I_{PD} - I_E$). In one or more alternative embodiments, the notification application 712 may automatically instruct, signal, or otherwise command the command generation application 714 to initiate recommended remedial action (e.g., suspending or reducing delivery) concurrently to generating an alert (or in some embodiments, in lieu of generating an alert).

In one embodiment, if the amount of excess insulin corresponds to the basal infusion over a period of time, the notification application 712 may calculate or otherwise determine a recommended amount of time for which the basal infusion should be suspended to cancel out or negate the excess insulin and automatically generate a user notification via the user interface 540, 708 that indicates the recommended amount of time the basal infusion should be suspended to reduce the likelihood of an excess insulin condition. In response to the notification, the user may manipulate user interface 540, 708 to instruct the pump control system 520, 700 and/or the command generation application 714 to suspend the basal infusion for the recommended duration of time. Alternatively, the notification application 712 may calculate or otherwise determine a recommended amount of by which the basal infusion deliveries should be reduced over a particular amount of time to cancel out or negate the excess insulin and automatically generate a user notification via the user interface 540, 708 that indicates the recommended reduced basal infusion rate for a recommended duration of time. In an alternative embodiment, the notification application 712 may automatically signal, command, or otherwise instruct the command generation application 714 to suspend or otherwise disable the amount of scheduled deliveries, or alternatively reduce the scheduled delivery amounts, by an amount of time required to offset the excess insulin and generate or otherwise provide a user notification indicating that delivery is temporarily being suspended or reduced. For example, if the amount of excess insulin corresponds to the basal infusion over a period of time (e.g., 30 minutes), the notification application 712 may automatically signal the command generation application 714 to suspend the basal infusion for that amount of time and generate a user notification via the user interface 540, 708 that indicates the basal infusion is being suspended for that amount of time.

When the amount of excess insulin is greater than the amount of insulin pending delivery (e.g., $I_E > I_{PD}$) or the user prefers not to suspend delivery, the notification application 712 calculates or otherwise determines a recommended amount of carbohydrates to be consumed to offset the excess insulin. For example, the notification application 712 may utilize the user's current insulin to carbohydrate ratio used for determining meal-related boluses to convert the excess insulin to a recommended amount of carbohydrates ($C_R$) using the equation $C_R = R_{12} I_E$, where $R_{12}$ is the user's current carbohydrate ratio used for bolusing meals in grams per unit of insulin. Thereafter, the notification application 712 may automatically generate or otherwise provide a notification of the recommended amount of carbohydrates to the user, for example, by displaying the recommended amount of carbohydrates on the user interface 540, 708 or a display associated with another device within the infusion system 100.

In some embodiments, the notification application 712 may determine the recommended amount of carbohydrates in combination with suspending scheduled insulin deliveries. For example, the notification application 712 may identify or otherwise determine scheduled insulin deliveries that can be canceled to offset the excess insulin by a first amount, and then convert the remaining excess insulin to a recommended amount of carbohydrates. In the case where the notification application 712 determines that all of the scheduled insulin deliveries should be suspended to offset the excess insulin by the amount of insulin pending delivery, the remaining amount of excess insulin may be converted to a recommended amount of carbohydrates (e.g., $C_R = R_{12}(I_E - I_{PD})$). In such embodiments, the notification application 712 may notify the user that the future insulin delivery should be suspended for a desired amount of time (or reduced by a desired amount) in combination with the user consuming the recommended amount of carbohydrates to entirely offset the estimated amount of excess insulin in combination with the reduced amount of insulin pending delivery.

In yet other embodiments, the notification application 712 may calculate or otherwise determine a recommended dosage of glucagon (or another suitable glucose stimulant) based on the amount of excess insulin. In this regard, the notification application 712 may determine an estimated glucose drop based on the amount of excess insulin and the user's current insulin sensitivity factor, calculate or otherwise determine a recommended amount of glucagon that would cancel or otherwise offset the estimated glucose drop, and generate or otherwise provide a notification of the recommended dosage to the user. In embodiments where the infusion device 502 is capable of delivering both insulin and glucagon, the notification application 712 may notify the pump control system 520 to automatically deliver the recommended amount of glucagon.

Still referring to FIG. 10, the loop defined by tasks 1002, 1004, 1006, 1008, 1010, 1012 and 1014 may repeat throughout operation of the infusion device 102, 200, 502 to continuously monitor the user's current and anticipated IOB to identify when an excessive amount of insulin may be delivered to the user. In this regard, since the infusion device 102, 200, 502 cannot remove insulin from the body of the user, providing advance notifications of a potential excess insulin condition allows remedial action to be taken before a hypoglycemic event or other undesirably low glucose level. For example, even though the user's current glucose measurement value may be above a target value and/or trending above the target value such that the user's predicted glucose level may indicate a potential hyperglycemic event, the notification application 712 may identify that the user's glucose level is actually likely to fall below a desired level based on the total amount of insulin that will eventually be metabolized by the user by accounting for the user's current IOB and already commanded or scheduled insulin deliveries. Thus, the user may be notified of a potential excess insulin condition well in advance while the user's current and/or predicted glucose levels indicate that a hypoglycemic event is unlikely or even that additional insulin may be desired, thereby providing the user with ample time to remedy the imbalance and avoid a potential hypoglycemic event or excess insulin condition. For example, in contrast to existing alerting schemes for warning a user of hypoglycemia (or impending hypoglycemia) based solely on the sensor glucose measurements, the excess insulin alerting process 1000 may notify the user when it becomes apparent that the amount of insulin infused is more than required (e.g., when the user overestimates carbohydrates in a meal) rather than waiting until the glucose measurement values have dropped sufficiently over a long enough period of time to indicate an actual (or impending) hypoglycemic event.

It should be noted that the excess insulin alerting process 1000 may also be performed whenever a new blood glucose measurement is obtained via the blood glucose meter 530 in lieu of the sensor glucose measurement value from the sensing arrangement 504, 600. In this regard, the estimated amount of excess insulin may be determined using the equation $$I_E = \max\left(\frac{G_T - (G_B - I_{SF}(I_{OB} + I_{PD}))}{I_{SF}}, 0\right),$$

where $G_B$ is the blood glucose measurement from the blood glucose meter 530. In such embodiments, the excess insulin alerting process 1000 may also determine recommended modifications to the basal infusion schedule or other scheduled deliveries and/or determine a recommended amount of carbohydrates to be consumed and provide appropriate user notifications in a similar manner as described above. Thus, the excess insulin alerting process 1000 may complement correction bolus determinations to better avoid excess insulin conditions. Additionally, in some alternative embodiments, in response to determining the excess insulin is greater than zero based on the user's current glucose measurement value from the sensing arrangement 504, 600 (e.g., task 1014), the excess insulin alerting process 1000 may generate an alert that prompts the user to obtain a new blood glucose measurement value before determining any recommended actions. Thereafter, in response to receiving a new blood glucose measurement value from the blood glucose meter 530, the notification application 712 and/or the excess insulin alerting process 1000 may determine a recommended remedial action using the new blood glucose measurement value and provide a notification of the recommended remedial action (e.g., tasks 1016, 1018). In this regard, blood glucose measurement values obtained via a blood glucose meter 530 are generally more accurate or reliable than interstitial fluid glucose measurement values obtained from the sensing arrangement 504, 600, and thus, prompting the user for a new blood glucose measurement value before determining the recommended action improves the quality of the recommendation.

Figure 11:
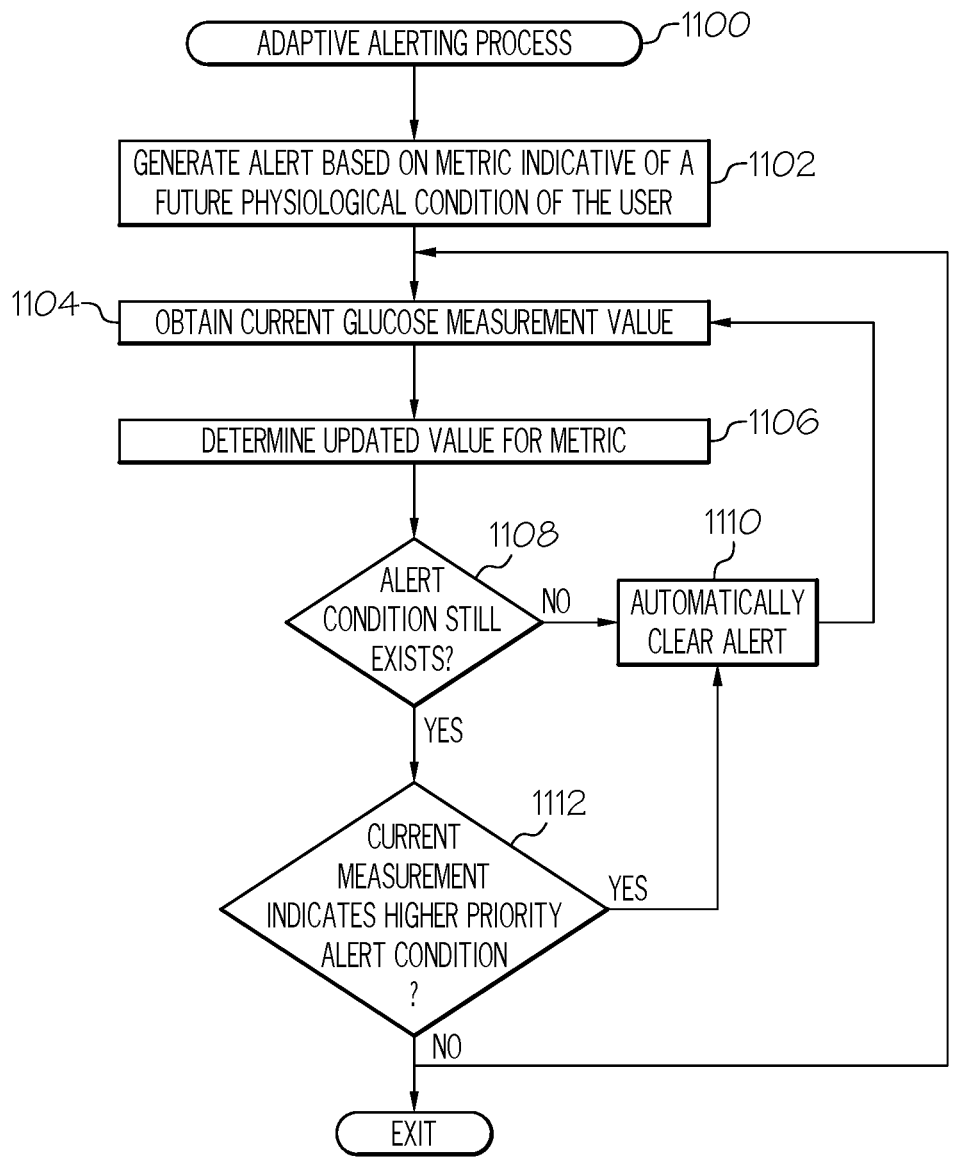
FIG. 11 is a flow diagram of an exemplary adaptive alerting process suitable for use with the control system of FIG. 5 in conjunction with one or more of the processes of FIGS. 8-10.

FIG. 11 depicts an exemplary adaptive alerting process 1100 suitable for implementation by a control system associated with a fluid infusion device to automatically clear alerts that become non-actionable or are superseded by other alerts. The various tasks performed in connection with the adaptive alerting process 1100 may be performed by hardware, firmware, software executed by processing circuitry, or any combination thereof. For illustrative purposes, the following description refers to elements mentioned above in connection with FIGS. 1-7. In practice, portions of the adaptive alerting process 1100 may be performed by different elements of the control system 500, such as, for example, the infusion device 502, the sensing arrangement 504, 600, the pump control system 520, 700, the notification application 712, the command generation application 714, and/or the user interface 540, 708. It should be appreciated that the adaptive alerting process 1100 may include any number of additional or alternative tasks, the tasks need not be performed in the illustrated order and/or the tasks may be performed concurrently, and/or the adaptive alerting process 1100 may be incorporated into a more comprehensive procedure or process having additional functionality not described in detail herein. Moreover, one or more of the tasks shown and described in the context of FIG. 11 could be omitted from a practical embodiment of the adaptive alerting process 1100 as long as the intended overall functionality remains intact.

The illustrated process 1100 begins by generating or otherwise providing an alert based on a metric indicative of a future physiological condition of a user (task 1102). As described above in the context of FIGS. 8-10, the notification application 712 may calculate or otherwise determine a value for a homeostasis metric indicative of the user's glucose level and generate a notification indicative of a potential remedial action in a manner that is influenced by the value for the homeostasis metric. For example, as described above in the context of the correction bolus alerting process 800 of FIG. 8, the notification application 712 may calculate or otherwise determine an estimated correction bolus amount based on the user's current glucose measurement, current IOB, current insulin sensitivity factor, currently pending insulin deliveries, and a target value and generate or otherwise provide a notification indicative of a recommended correction bolus based on the estimated correction bolus amount indicating the user's glucose level exceeds the target value by at least a threshold amount. In another embodiment, as described above in the context of the anomalous response alerting process 900 of FIG. 9, the notification application 712 may generate or otherwise provide a notification based on a difference between an expected glucose measurement value and the user's current glucose measurement value. As yet another example, the notification application 712 may calculate or otherwise determine an estimated amount of excess insulin and generate or otherwise provide a notification indicative of a recommended remedial action for mitigating the potential excess insulin condition, as described above in the context of process 1000 of FIG. 10.

The adaptive alerting process 1100 continues by obtaining an updated measurement value for the physiological condition of the user (task 1104) and automatically clearing the initial alert in a manner that is influenced by the updated measurement value. In exemplary embodiments, the adaptive alerting process 1100 calculates or otherwise determines an updated homeostasis metric based on the updated current measurement value for the user and automatically clears the alert in response to determining that the alert condition no longer exists based on the updated homeostasis metric (tasks 1106, 1108, 1110). In this regard, when the user's most recent measurement value indicates the alert condition is no longer likely and therefore no remedial action is required at the current point in time, the notification application 712 ceases providing the alert via the user interface 540, 708. For example, if the alert is realized as a graphical representation of a recommended correction bolus, a recommended amount of carbohydrates, or the like that is displayed on a display associated with the infusion device 102, 200, 502, the notification application 712 may automatically remove the displayed recommendation from the display. Similarly, if the alert is realized as an illuminated display element (e.g., a light-emitting diode indicator), the notification application 712 may automatically cause the pump control system 520, 700 to cease illumination of the display element. Likewise, if the alert includes or is otherwise realized as an auditory notification (e.g., a periodic beeping), the notification application 712 may automatically cause the pump control system 520, 700 to cease providing the auditory alert.

For example, referring to correction bolus alerting process 800, the notification application 712 may calculate or otherwise determine an initial estimated correction bolus amount based on the user's current glucose measurement at an initial point in time, the user's current IOB at that time, the user's current insulin sensitivity factor at that time, the pending insulin deliveries for the user at that time, and a target value. When that initial estimated correction bolus amount exceeds the alert threshold, the notification application 712 may generate or otherwise provide a notification indicative of a potential insufficient insulin condition by displaying or otherwise presenting the recommended correction bolus equal to the initial estimated correction bolus amount. Thereafter, in response to receiving an updated glucose measurement for the user from the sensing arrangement 504, 600 at a subsequent point in time, the notification application 712 calculates an updated estimated correction bolus amount based on the user's current glucose measurement at that subsequent time, the user's current IOB at that subsequent time, the user's current insulin sensitivity factor at that subsequent time, the pending insulin deliveries for the user at that subsequent time, and the target value. When the user's current glucose measurement at that subsequent time has fallen to a level such that the updated estimated correction bolus amount is less than the alert threshold after accounting for any changes in the user's IOB and pending insulin deliveries, the notification application 712 determines that the potential insufficient insulin condition no longer exists and automatically stops displaying indication of the recommended correction bolus. In this manner, once the recommended correction bolus alert is no longer actionable, it is automatically cleared or otherwise removed from presentation to the user. For example, the command generation application 714 may generate one or more delivery commands to deliver a dosage of insulin to the user based on the initial glucose measurement value, and after operating the motor 510 of the infusion device 502 to deliver at least a portion of the dosage, the user's current glucose measurement at a subsequent time in conjunction with the increases in the user's current IOB and/or pending deliveries based on the initial glucose measurement value may indicate that the recommended correction bolus alert is no longer necessary since the infusion delivery scheme has sufficiently compensated for the user's glucose measurement value(s).

Similarly, referring to anomalous response alerting process 900, the notification application 712 may calculate or otherwise determine an initial difference between the user's expected glucose level and the user's current glucose measurement at an initial point in time and generate or otherwise provide a notification indicative of a potential anomalous condition when the initial difference indicates the insulin is not having the desired effectiveness. Thereafter, in response to receiving an updated glucose measurement for the user from the sensing arrangement 504, 600 at a subsequent point in time, the notification application 712 calculates an updated expected glucose level for that subsequent time. When the user's current glucose measurement at that subsequent time has fallen to a level such that the difference between the updated expected glucose level and the user's current glucose measurement value is less than the alert threshold, the notification application 712 determines that the potential anomalous condition no longer exists and automatically stops displaying indication of the anomalous condition. In this manner, once it appears that the infused insulin and the infusion device 102, 200, 502 are functioning as expected, the potential anomalous condition alerts is no longer actionable and is automatically cleared or otherwise removed from presentation to the user.

Likewise, referring to process 1000, the notification application 712 may calculate or otherwise determine an initial excess insulin amount based on the user's current glucose measurement at an initial point in time, the user's current IOB and insulin sensitivity at that time, the pending insulin deliveries for the user at that time, and a threshold alerting value. When the notification application 712 identifies a potential excess insulin condition, the notification application 712 may generate or otherwise provide a notification indicative of a potential excess insulin condition by displaying or otherwise presenting a recommended amount of carbohydrates to consume to offset the excess insulin, recommended modifications to the pending insulin deliveries, or the like. Thereafter, in response to receiving an updated glucose measurement for the user from the sensing arrangement 504, 600 at a subsequent point in time, the notification application 712 calculates an updated excess insulin amount. In this regard, the updated excess insulin amount is calculated based on the current glucose measurement at that subsequent time, the current IOB at that subsequent time, the current insulin sensitivity factor at that subsequent time, the pending insulin deliveries at that subsequent time, and the threshold alerting value. The notification application 712 determines that the potential excess insulin condition no longer exists when the user's current glucose measurement at that subsequent time has risen to a level (or failed to drop as much as anticipated based on the user's previous IOB) such that the updated excess insulin amount is less than or equal to zero. In response, the notification application 712 automatically stops displaying indication of the recommended remedial action(s). In this manner, once the excess insulin alert is no longer actionable, it is automatically cleared or otherwise removed from presentation to the user.

Referring again to FIG. 11, in exemplary embodiments, the adaptive alerting process 1100 also automatically clears the initial alert when the updated measurement value is indicative of a higher priority or higher severity alert condition having the same root cause as the initial alert (task 1112). In this regard, when a potential condition attempted to be prevented by preemptive alerting actual exists, the preemptive alerts are redundant. Accordingly, the alerts are automatically cleared to improve the user experience and make it easier for the user to identify which alerts are important and what actions should be taken. For example, when an updated glucose measurement value for the user is greater than a hyperglycemic threshold value, the notification application 712 may automatically clear the recommended correction bolus alert for the potential insufficient insulin condition and automatically stops displaying indication of the recommended correction bolus. In this manner, once the recommended correction bolus alert is redundant or superseded by a more significant alert condition, it is automatically cleared or otherwise removed from presentation to the user. A more escalated or emergent alert (e.g., a hyperglycemic alert) may be presented for the more significant alert condition in lieu of the preemptive alert to more effectively notify the user of the change in the user's physiological condition having the same root cause as a previous alert. Similarly, if the updated glucose measurement value for the user is greater than a hyperglycemic threshold value, the notification application 712 may automatically clear the notification of a potential anomalous condition based on the user's glucose measurement values indicating the infused insulin is not having the anticipated effect. Likewise, if the updated glucose measurement value for the user is less than a hypoglycemic threshold value, the notification application 712 may automatically clear the excess insulin alert and automatically stops displaying indication of the recommended remedial actions for the potential excess insulin condition. Again, once the excess insulin alert is redundant or superseded by a more significant alert condition, the notification application 712 may automatically clear the excess insulin alert from presentation to the user in favor of an escalated hypoglycemic alert.

It should be noted that although the adaptive alerting process 1100 may be described in the context of the alerts described in the context of FIGS. 8-10, the adaptive alerting process 1100 is not limited to any particular type of alert. For example, the adaptive alerting process 1100 may be implemented in an equivalent manner for alerts generated based on predicted glucose values for the user. For example, a glucose measurement value from the body 501 of the user may be obtained from the sensing arrangement 504, 600 at a first time, and an initial predicted glucose value for the user may be calculated based on that current glucose measurement value and its preceding glucose measurement values. When the initial predicted glucose value is violates an alerting threshold (e.g., greater than a hyperglycemia alert threshold or less than a hypoglycemia alert threshold), the adaptive alerting process 1100 may automatically provide an alert indicating a predicted hyperglycemic event or a predicted hypoglycemic event to the user via the user interface 540, 708. Thereafter, a subsequent glucose measurement value may be obtained from the sensing arrangement 504, 600 at a subsequent time, and an updated predicted glucose value for the user may be calculated based on that newer glucose measurement value and its preceding glucose measurement values. When the updated predicted glucose value no longer violates an alerting threshold, the adaptive alerting process 1100 may automatically clear the alert that indicated a predicted hyperglycemic event or a predicted hypoglycemic event. Similarly, if the newer glucose measurement value is greater than a hyperglycemia alerting threshold or is less than a hypoglycemia alerting threshold, the adaptive alerting process 1100 may automatically clear or otherwise remove the alert indicating a predicted event and provide the appropriate alert indicating the actual hyperglycemic event or hypoglycemic event in lieu of the predictive alert.

To briefly summarize, the subject matter described herein facilitates generating actionable alerts in a preemptive manner before an undesired event occurs and provide appropriate recommended actions that may be performed by a user to mitigate or otherwise avoid the potential undesired event. For example, the correction bolus alerting process 800 may recommend a correction bolus having an amount that is calculated to regulate the user's glucose level to a particular target glucose value (or within a threshold deviation of the target value) in advance of any actual or predicted hyperglycemic events. Similarly, the excess insulin alerting process 800 may recommend an amount of carbohydrates to be consumed by the user and/or recommend modifications to the insulin delivery scheme (e.g., temporarily reduced or suspended basal infusion deliveries) in advance of any actual or predicted hypoglycemic events. The alerts may also be automatically cleared in response to changes to the values of the underlying metrics upon which the alerts were generated or in response to being superseded by higher severity (or higher priority) alerts with the same root cause, such that the user is no longer presented with an alert once it becomes non-actionable or redundant. By dynamically and adaptively generating alerts based on an anticipated future physiological condition of a user in a manner that accounts for the real-time relationship between the current glucose measurement values, the current IOB, the pending future insulin deliveries, and the current insulin sensitivity factor, the user may be reliably provided with actionable alerts and corresponding recommended remedial actions in a manner that provides sufficient time for the user to remedy and avoid a potentially adverse physiological condition.

For the sake of brevity, conventional techniques related to glucose sensing and/or monitoring, closed-loop glucose control, predictive glucose management, sensor calibration and/or compensation, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. An infusion system comprising:
   one or more processors; and
   one or more processor-readable storage media storing instructions which, when executed by the one or more processors, cause performance of:
   obtaining a current glucose measurement value of a user from a sensing arrangement;
   obtaining a determination of a current amount of active insulin in the body of the user;
   identifying an amount of future insulin deliveries to be delivered by an infusion device;
   determining a homeostasis metric based at least in part on the current glucose measurement value, the current amount of active insulin in the body of the user, and the amount of future insulin deliveries, wherein determining the homeostasis metric comprises predicting a change in the current glucose measurement value based on accounting for metabolism of the current amount of active insulin and the amount of future insulin deliveries; and
   generating an alert based at least in part on the homeostasis metric.

2. The infusion system of claim 1, wherein:
   the homeostasis metric comprises an estimated correction bolus amount determined based at least in part on the current amount of active insulin in the body of the user, the current glucose measurement value, the amount of future insulin deliveries, and a target glucose value; and
   the alert comprises a graphical notification of the estimated correction bolus amount.

3. The infusion system of claim 1, wherein:
   the homeostasis metric comprises an excess insulin amount determined based at least in part on the current amount of active insulin in the body of the user, the current glucose measurement value, the amount of future insulin deliveries, and a target glucose value; and
   the alert comprises a graphical notification of a recommended amount of carbohydrates to offset the excess insulin amount.

4. The infusion system of claim 1, wherein the homeostasis metric comprises an estimated correction bolus amount determined based at least in part on the current amount of active insulin in the body of the user, the current glucose measurement value, the amount of future insulin deliveries, and a target glucose value, and wherein the one or more processor-readable storage media further store instructions which, when executed by the one or more processors, cause performance of adjusting the homeostasis metric by multiplying the estimated correction bolus amount by a trend adjustment factor.

5. The infusion system of claim 4, wherein the one or more processor-readable storage media further store instructions which, when executed by the one or more processors, cause performance of determining the trend adjustment factor based on a difference between the measurement value and a preceding measurement value.

6. The infusion system of claim 4, wherein generating the alert comprises generating the alert when the estimated correction bolus amount is greater than an alert threshold value.

7. The infusion system of claim 1, wherein the one or more processor-readable storage media further store instructions which, when executed by the one or more processors, cause performance of suppressing or disabling the alert when a predicted value for a glucose level of the user exceeds an upper threshold value and the homeostasis metric is less than an alert threshold value.

8. The infusion system of claim 1, wherein the one or more processor-readable storage media further store instructions which, when executed by the one or more processors, cause performance of, after automatically generating the alert, obtaining a second measurement value for the physiological condition from the sensing arrangement and automatically clearing the alert based at least in part on the second measurement value.

9. The infusion system of claim 8, wherein automatically clearing the alert comprises automatically clearing the alert when the second measurement value is greater than a hyperglycemic alert threshold.

10. The infusion system of claim 9, wherein the one or more processor-readable storage media further store instructions which, when executed by the one or more processors, cause performance of automatically providing a hyperglycemic alert in lieu of the alert when the second measurement value is greater than the hyperglycemic alert threshold.

11. The infusion system of claim 8, wherein automatically clearing the alert comprises automatically clearing the alert when the second measurement value is less than a hypoglycemic alert threshold.

12. The infusion system of claim 11, wherein the one or more processor-readable storage media further store instructions which, when executed by the one or more processors, cause performance of, automatically providing a hypoglycemic alert in lieu of the alert when the second measurement value is less than the hypoglycemic alert threshold.

13. The infusion system of claim 8, wherein the one or more processor-readable storage media further store instructions which, when executed by the one or more processors, cause performance of operating the infusion device to deliver a dosage of the insulin to the user based at least in part on the current glucose measurement value, wherein the second measurement value is obtained after operating the infusion device to deliver the dosage.

14. The infusion system of claim 1, wherein the homeostasis metric comprises an estimated correction bolus amount for maintaining the user's future glucose level at or near a target glucose level.

15. The infusion system of claim 14, wherein the estimated correction bolus amount is indicative of whether the user needs additional insulin to account for carbohydrates consumed by the user to maintain his or her glucose level at or near the target glucose level.

16. The infusion system of claim 1, wherein the homeostasis metric comprises an expected glucose measurement value at a subsequent time after a correction bolus indicative of whether the correction bolus is having its anticipated effect on the user's glucose level.

17. The infusion system of claim 1, wherein the homeostasis metric comprises an estimated amount of excess insulin determined based on an expected glucose measurement value after all delivered insulin is metabolized.

18. An infusion device comprising:
   a motor operable to deliver insulin to a body of a user, the insulin influencing a physiological condition of the user; and
   a control system coupled to the motor and configured to:
   operate the motor to deliver the insulin;
   obtain a current glucose measurement value for the physiological condition in the body of the user;
   determine a current amount of active insulin in the body of the user;

identify an amount of future insulin deliveries to be delivered by the infusion device;

determine a homeostasis metric based at least in part on the current amount of active insulin in the body of the user, the amount of future insulin deliveries, and the current glucose measurement value, wherein determining the homeostasis metric comprises predicting a change in the current glucose measurement value based on accounting for metabolism of the current amount of active insulin and the amount of future insulin deliveries; and provide a notification based at least in part on the homeostasis metric.

19. One or more non-transitory processor-readable storage media storing instructions which, when executed by the one or more processors, cause performance of:

obtaining a current glucose measurement value of a user from a sensing arrangement;

obtaining a determination of a current amount of active insulin in the body of the user;

identifying an amount of future insulin deliveries to be delivered by an infusion device;

determining a homeostasis metric based at least in part on the current glucose measurement value, the current amount of active insulin in the body of the user, and the amount of future insulin deliveries, wherein determining the homeostasis metric comprises predicting a change in the current glucose measurement value based on accounting for metabolism of the current amount of active insulin and the amount of future insulin deliveries; and generating an alert based at least in part on the homeostasis metric.

* * * * *